US012590338B2

(12) United States Patent
Fang et al.

(10) Patent No.: US 12,590,338 B2
(45) Date of Patent: Mar. 31, 2026

(54) METHOD AND DEVICE FOR DETECTION OF AMPICILLIN-RESISTANT NON-TYPHOIDAL *Salmonella*

(71) Applicant: TAIPEI MEDICAL UNIVERSITY, Taipei (TW)

(72) Inventors: Shiuh-Bin Fang, New Taipei (TW); Wei-Chiao Chang, New Taipei (TW); Wan-Hsuan Chou, Taipei (TW); Ke-Chuan Wang, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 134 days.

(21) Appl. No.: 17/057,625

(22) PCT Filed: May 21, 2019

(86) PCT No.: PCT/CN2019/087834
§ 371 (c)(1),
(2) Date: Nov. 20, 2020

(87) PCT Pub. No.: WO2019/223694
PCT Pub. Date: Nov. 28, 2019

(65) Prior Publication Data
US 2021/0285028 A1 Sep. 16, 2021

Related U.S. Application Data

(60) Provisional application No. 62/674,180, filed on May 21, 2018.

(51) Int. Cl.
*C12Q 1/689* (2018.01)

(52) U.S. Cl.
CPC ....... *C12Q 1/689* (2013.01); *C12Q 2600/106* (2013.01); *C12Q 2600/158* (2013.01)

(58) Field of Classification Search
CPC .............. C12Q 1/689; C12Q 2600/106; C12Q 2600/158
See application file for complete search history.

(56) References Cited

PUBLICATIONS

Definition of "device" (1 page), Merriam-Webster Dictionary, merriam-webster.com/dictionary/device (downloaded Sep. 20, 2022). (Year: 2022).*
Kudirkiene, E. et al. Frontiers in Microbiology 9:1010 (14 pages) (doi: 10.3389/fmicb.2018.01010). May 17, 2018. (Year: 2018).*
Qiao, J. et al. International Journal of Food Microbiology 248:72 (Feb. 2017). (Year: 2017).*
Dione, M.M. et al. PLoS Neglected Tropical Diseases 5(5):e114 (7 pages). (May 2011) (Year: 2011).*
Chuang, Y-C et al. Journal of Food Protection 71(6):1108. (Year: 2008).*

(Continued)

*Primary Examiner* — Diana B Johannsen
(74) *Attorney, Agent, or Firm* — Birch, Stewart, Kolasch & Birch, LLP

(57) ABSTRACT

Disclosed is a method and a device for determining whether a sample contains ampicillin-resistant (AMP-R) non-typhoid *Salmonella* (NTS). The method comprises detecting, in the sample, the presence of a combination of certain genes or their gene products, wherein the presence of said combination indicates the sample contains AMP-R NTS.

10 Claims, 1 Drawing Sheet
Specification includes a Sequence Listing.

(56)            References Cited

PUBLICATIONS

Bae, D. et al. International Journal of Food Microbiology 214;12 (Jul. 2015). (Year: 2015).*
Ahmed, A.M. et al. Journal of Antimicrobial Chemotherapy 55:371. (Year: 2005).*
Dierikx, C. et al. Veterinary Microbiology 145:273-278. (Year: 2010).*

* cited by examiner

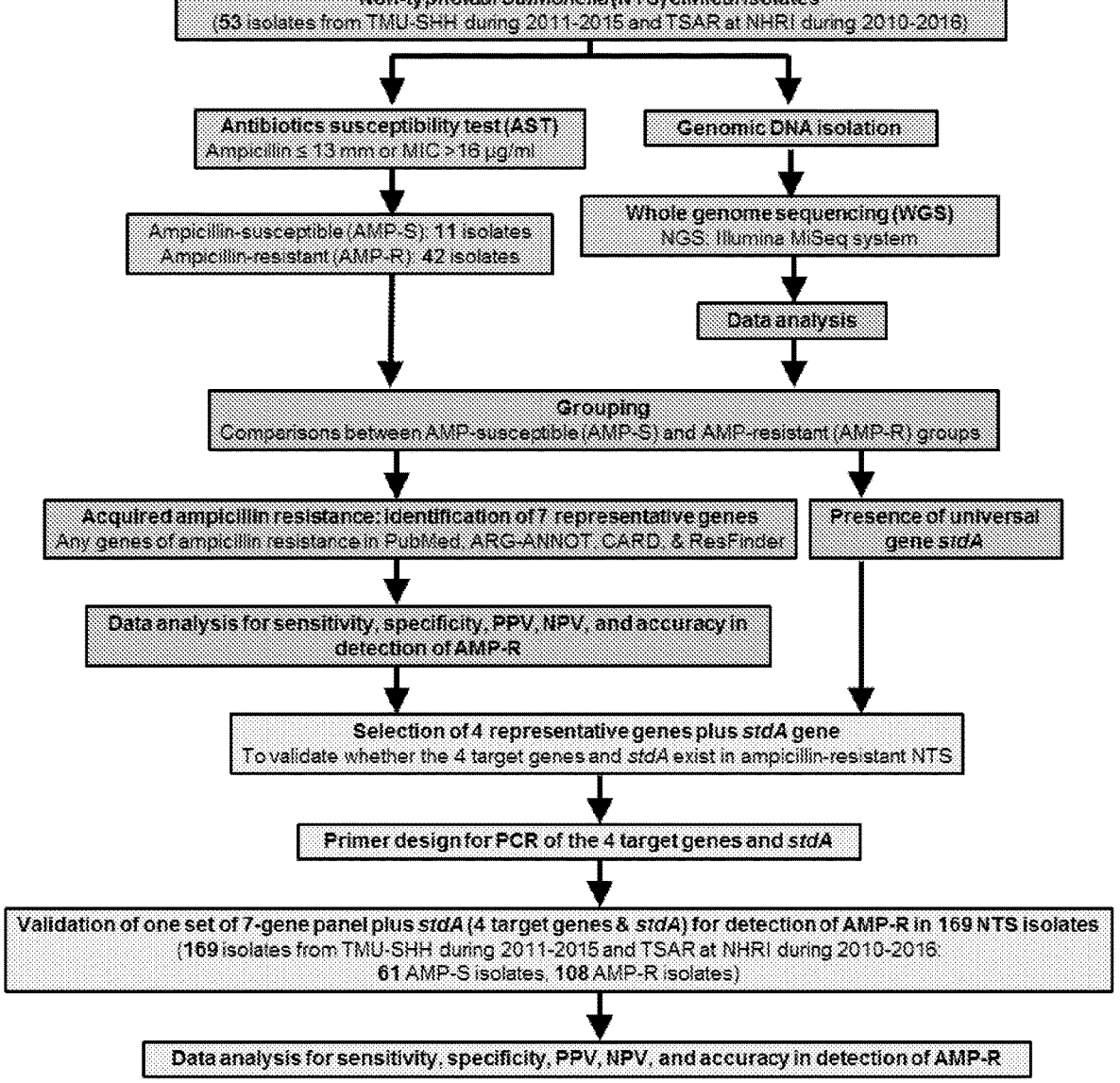

SEQUENCE LISTING

<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: PCR primer

<400> SEQUENCE: 1
acgctcgtcg tttggtatg                                          19

-continued

<210> SEQ ID NO 2
<211> LENGTH: 19
<212> TYPE: DNA
<213> ORGANISM: Artificial Sequence
<220> FEATURE:
<223> OTHER INFORMATION: PCR primer

<400> SEQUENCE: 2
tgctatgtgg tgcggtatt                                                19

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
tagaaaagca agtagggcag g                                             21

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
agatagcgcg gaaccaaata a                                             21

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
cgcagaacga acaaaaagat                                               20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
aatacgccag tagcgagact                                               20

<210> SEQ ID NO 7
<211> LENGTH: 18
<212> TYPE: DNA
<213> ORGANISM: Artificial Sequence
<220> FEATURE:
<223> OTHER INFORMATION: PCR primer

<400> SEQUENCE: 7
tgagccacac ctggatta                                                 18

<210> SEQ ID NO 8
<211> LENGTH: 18
<212> TYPE: DNA
<213> ORGANISM: Artificial Sequence
<220> FEATURE:
<223> OTHER INFORMATION: PCR primer -continued

<400> SEQUENCE: 8
ccctgccgca gatttttta                                             18

<210> SEQ ID NO 9
<211> LENGTH: 23
<212> TYPE: DNA
<213> ORGANISM: Artificial Sequence
<220> FEATURE:
<223> OTHER INFORMATION: PCR primer

<400> SEQUENCE: 9
tcacaggtat ttcagagtgt agg                                        23

<210> SEQ ID NO 10
<211> LENGTH: 22
<212> TYPE: DNA
<213> ORGANISM: Artificial Sequence
<220> FEATURE:
<223> OTHER INFORMATION: PCR primer

<400> SEQUENCE: 10
cagtcgatcc accaacagca gg                                         22

<210> SEQ ID NO 11
<211> LENGTH: 861
<212> TYPE: DNA
<213> ORGANISM: Artificial Sequence
<220> FEATURE:
<223> OTHER INFORMATION: blaTEM-1B

<400> SEQUENCE: 11
atgagtattc aacatttccg tgtcgccctt attcccttttt ttgcggcatt ttgccttcct    60
gtttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggtgc ggtattatcc   240
cgtgttgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgctgcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga caccacgatg   540
cctgcagcaa tggcaacaac gttgcgcaaa ctattaactg gcgaactact tactctagct   600
tcccggcaac aattaataga ctggatggag gcggataaag ttgcaggacc acttctgcgc   660
tcggcccttc cggctggctg gtttattgct gataaatctg gagccggtga gcgtgggtct   720
cgcggtatca ttgcagcact ggggccagat ggtaagccct cccgtatcgt agttatctac   780
acgacgggga gtcaggcaac tatggatgaa cgaaatagac agatcgctga gataggtgcc   840
tcactgatta agcattggta a                                        861

<210> SEQ ID NO 12
<211> LENGTH: 831
<212> TYPE: DNA
<213> ORGANISM: Artificial Sequence
<220> FEATURE:
<223> OTHER INFORMATION: blaOXA-1

<400> SEQUENCE: 12

-continued

```
atgaaaaaca caatacatat caacttcgct attttttttaa taattgcaaa tattatctac      60
agcagcgcca gtgcatcaac agatatctct actgttgcat ctccattatt tgaaggaact     120
gaaggttgtt ttttactttta cgatgcatcc acaaacgctg aaattgctca attcaataaa     180
gcaaagtgtg caacgcaaat ggcaccagat tcaactttca agatcgcatt atcacttatg     240
gcatttgatg cggaaataat agatcagaaa accatattca aatgggataa aaccccaaa     300 ggaatggaga tctggaacag caatcataca ccaaagacgt ggatgcaatt ttctgttgtt     360
tgggtttcgc aagaaataac ccaaaaaatt ggattaaata aaatcaagaa ttatctcaaa     420
gattttgatt atggaaatca agacttctct ggagataaag aaagaaacaa cggattaaca     480
gaagcatggc tcgaaagtag cttaaaaatt tcaccagaag aacaaattca attcctgcgt     540
aaaattatta atcacaatct cccagttaaa aactcagcca tagaaaacac catagagaac     600
atgtatctac aagatctgga taatagtaca aaactgtatg ggaaaactgg tgcaggattc     660
acagcaaata gaaccttaca aaacggatgg tttgaagggt ttattataag caaatcagga     720
cataaatatg tttttgtgtc cgcacttaca ggaaacttgg ggtcgaattt aacatcaagc     780
ataaaagcca agaaaaatgc gatcaccatt ctaaacacac taaatttata a             831
```

```
<210> SEQ ID NO 13
<211> LENGTH: 867
<212> TYPE: DNA
<213> ORGANISM: Artificial Sequence
<220> FEATURE:
<223> OTHER INFORMATION: blaCARB-2

<400> SEQUENCE: 13
atgaagtttt tattggcatt ttcgctttta ataccatccg tggttttttgc aagtagttca      60 aagtttcagc aagttgaaca agacgttaag gcaattgaag tttctctttc tgctcgtata     120
ggtgtttccg ttcttgatac tcaaaatgga gaatattggg attacaatgg caatcagcgc     180
ttcccgttaa caagtacttt taaaacaata gcttgcgcta aattactata tgatgctgag     240
caaggaaaag ttaatcccaa tagtacagtc gagattaaga aagcagatct tgtgacctat     300
tcccctgtaa tagaaaagca agtagggcag gcaatcacac tcgatgatgc gtgcttcgca     360
actatgacta caagtgataa tactgcggca aatatcatcc taagtgctgt aggtggcccc     420
aaaggcgtta ctgattttt aagacaaatt ggggacaaag agactcgtct agaccgtatt     480
gagcctgatt taaatgaagg taagctcggt gatttgaggg atacgacaac tcctaaggca     540
atagccagta ctttgaataa attttttattt ggttccgcgc tatctgaaat gaaccagaaa     600
aaattagagt cttggatggt gaacaatcaa gtcactggta atttactacg ttcagtattg     660
ccggcgggat ggaacattgc ggatcgctca ggtgctggcg gatttggtgc tcggagtatt     720
acagcagttg tgtggagtga gcatcaagcc ccaattattg tgagcatcta tctagctcaa     780
acacaggctt caatggcaga gcgaaatgat gcgattgtta aaattggtca ttcaattttt     840 gacgttata catcacagtc gcgctga                                        867
```

```
<210> SEQ ID NO 14
<211> LENGTH: 861
<212> TYPE: DNA
<213> ORGANISM: Artificial Sequence
<220> FEATURE:
<223> OTHER INFORMATION: blaTEM-227

<400> SEQUENCE: 14
atgagtattc aacatttccg tgtcgcccctt attcccttttt ttgcggcatt ttgccttcct      60
```

-continued

```
gtttttgctc acccagaaac gctggtgaaa gtaaaagatg ctgaagataa gttgggtgca      120
cgagtgggtt acatcgagct ggatctcaac agcggtaaga tccttgagag ttttcgcccc      180
gaagaacgtt ttccaatgat gagcactttt aaagttctgc tatgtggtgc ggtattatcc      240
cgtgttgacg ccgggcaaga gcaactcggt cgccgcatac actattctca gaatgacttg      300
gttaagtact caccagtcac agaaaagcat cttacgaatg gcatgacagt aagagaatta      360
tgcagtgctg ccataaccat gagtgataac actgcggcca acttacttct gacaacgatc      420
ggaggaccga aggagctaac cgcttttttg cacaacatgg gggatcatgt aacccgcctt      480
gatcgttggg aaccggagct gaatgaagcc ataccaaacg acgagcgtga caccacgatg      540
cctgcagcaa tggcaacaac gttgcgcaaa ctattaactg gcgaactact tactctagct      600
tcccggcaac aattaataga ctggatggag gcggataaag ttgcaggacc acttctgcgc      660
tcggcccttc cggctggctg gtttattgct gataaatctg gagccagtga gcgtggatct      720
cgcggtatca ttgcagcact ggggccagat ggtaagccct cccgtatcgt agttatctac      780
acgacgggga gtcaggcaac tatggatgaa cgaaatagac agatcgctga gataggtacc      840
tcactgatta agcattggta a                                               861
```

```
<210> SEQ ID NO 15
<211> LENGTH: 1146
<212> TYPE: DNA
<213> ORGANISM: Artificial Sequence
<220> FEATURE:
<223> OTHER INFORMATION: blaCMY-2

<400> SEQUENCE: 15
```

```
atgatgaaaa aatcgttatg ctgcgctctg ctgctgacag cctctttctc cacatttgct       60
gccgcaaaaa cagaacaaca gattgccgat atcgttaatc gcaccatcac cccgttgatg      120
caggagcagg ctattccggg tatggccgtt gccgttatct accagggaaa accctattat      180
ttcacctggg gtaaagccga tatcgccaat aaccacccag tcacgcagca aacgctgttt      240
gagctaggat cggttagtaa gacgtttaac ggcgtgttgg gcggcgatgc tatcgcccgc      300
ggcgaaatta agctcagcga tccggtcacg aaatactggc cagaactgac aggcaaacag      360
tggcagggta tccgcctgct gcacttagcc acctatacgg caggcggcct accgctgcag      420
atccccgatg acgttaggga taaagccgca ttactgcatt tttatcaaaa ctggcagccg      480
caatggactc cgggcgctaa gcgactttac gctaactcca gcattggtct gtttggcgcg      540
ctggcggtga aaccctcagg aatgagttac gaagaggcaa tgaccagacg cgtcctgcaa      600
ccattaaaac tggcgcatac ctggattacg gttccgcaga cgaacaaaa agattatgcc      660 tggggctatc gcgaagggaa gcccgtacac gtttctccgg acaacttga cgccgaagcc      720 tatggcgtga atccagcgt tattgatatg gcccgctggg ttcaggccaa catggatgcc      780
agccacgttc aggagaaaac gctccagcag ggcattgcgc ttgcgcagtc tcgctactgg      840
cgtattggcg atatgtacca gggattaggc tgggagatgc tgaactggcc gctgaaagct      900
gattcgatca tcaacggcag cgacagcaaa gtggcattgg cagcgcttcc cgccgttgag      960
gtaaacccgc cgcccccgc agtgaaagcc tcatgggtgc ataaaacggg ctccactggt     1020
ggatttggca gctacgtagc cttcgttcca gaaaaaaacc ttggcatcgt gatgctggca     1080
aacaaaagct atcctaaccc tgtccgtgtc gaggcggcct ggcgcattct tgaaaagctg     1140
caataa                                                               1146
```

-continued

```
<210> SEQ ID NO 16
<211> LENGTH: 1146
<212> TYPE: DNA
<213> ORGANISM: Artificial Sequence
<220> FEATURE:
<223> OTHER INFORMATION: ampC

<400> SEQUENCE: 16
atgatgaaaa aatcgttatg ctgcgctctg ctgctgacag cctctttctc cacatttgct      60
gccgcaaaaa cagaacaaca gattgccgat atcgttaatc gcaccatcac cccgttgatg     120
caggagcagg ctattccggg tatggccgtt gccgttatct accagggaaa accctattat     180
ttcacctggg gtaaagccga tatcgccaat aaccacccag tcacgcagca aacgctgttt     240
gagctaggat cggttagtaa gacgtttaac ggcgtgttgg gcggcgatgc tatcgcccgc     300
ggcgaaatta agctcagcga tccggtcacg aaatactggc cagaactgac aggcaaacag     360
tggcagggta tccgcctgct gcacttagcc acctatacgg caggcggcct accgctgcag     420
atccccgatg acgttaggga taaagccgca ttactgcatt tttatcaaaa ctggcagccg     480
caatggactc cgggcgctaa gcgactttac gctaactcca gcattggtct gtttggcgcg     540
ctggcggtga aaccctcagg aatgagttac gaagaggcaa tgaccagacg cgtcctgcaa     600
ccattaaaac tggcgcatac ctggattacg gttccgcaga acgaacaaaa agattatgcc     660
tggggctatc gcgaagggaa gcccgtacac gtttctccgg gacgacttga cgccgaagcc     720
tatggcgtga aatccagcgt tattgatatg gcccgctggg ttcaggccaa catggatgcc     780
agccacgttc aggagaaaac gctccagcag ggcattgcgc ttgcgcagtc tcgctactgg     840
cgtattggcg atatgtacca gggattaggc tgggagatgc tgaactggcc gctgaaagct     900
gattcgatca tcaacggcag cgacagcaaa gtggcattgg cagcgcttcc cgccgttgag     960
gtaaacccgc cgcccccgc agtgaaagcc tcatgggtgc ataaaacggg ctccactggt    1020
ggatttggca gctacgtagc cttcgttcca gaaaaaaacc ttggcatcgt gatgctggca    1080
aacaaaagct atcctaaccc tgtccgtgtc gaggcggcct ggcgcattct tgaaaagctg    1140
caataa                                                            1146

<210> SEQ ID NO 17
<211> LENGTH: 876
<212> TYPE: DNA
<213> ORGANISM: Artificial Sequence
<220> FEATURE:
<223> OTHER INFORMATION: blaCTX-M-9

<400> SEQUENCE: 17
atggtgacaa agagagtgca acggatgatg ttcgcggcgg cggcgtgcat tccgctgctg      60
ctgggcagcg cgccgcttta tgcgcagacg agtgcggtgc agcaaaagct ggcggcgctg     120
gagaaaagca gcggagggcg gctgggcgtc gcgctcatcg ataccgcaga taatacgcag     180
gtgctttatc gcggtgatga acgctttcca atgtgcagta ccagtaaagt tatggcggcc     240
gcggcggtgc ttaagcagag tgaaacgcaa aagcagctgc ttaatcagcc tgtcgagatc     300
aagcctgccg atctggttaa ctacaatccg attgccgaaa aacacgtcaa cggcacaatg     360
acgctggcag agctgagcgc ggccgcgttg cagtacagcg acaataccgc catgaacaaa     420
ttgattgccc agctcggtgg cccggggaggc gtgacggctt ttgcccgcgc gatcggcgat     480
gagacgtttc gtctggatcg cactgaacct acgctgaata ccgccattcc cggcgacccg     540
agagacacca ccacgccgcg ggcgatggca cagacgttgc gtcagcttac gctgggtcat     600
```

-continued

```
gcgctgggcg aaacccagcg ggcgcagttg gtgacgtggc tcaaaggcaa tacgaccggc      660
gcagccagca ttcgggccgg cttaccgacg tcgtggactg caggtgataa gaccggcagc      720
ggcgactacg gcaccaccaa tgatattgcg gtgatctggc cgcagggtcg tgcgccgctg      780
gttctggtga cctattttac ccagccgcaa cagaacgcag agagccgccg cgatgtgctg      840
gcttcagcgg cgagaatcat cgccgaaggg ctgtaa                                876
```

```
<210> SEQ ID NO 18
<211> LENGTH: 861
<212> TYPE: DNA
<213> ORGANISM: Artificial Sequence
<220> FEATURE:
<223> OTHER INFORMATION: blaSHV-1

<400> SEQUENCE: 18
atgcgttata ttcgcctgtg tattatctcc ctgttagcca ccctgccgct ggcggtacac       60
gccagcccgc agccgcttga gcaaattaaa ctaagcgaaa gccagctgtc gggccgcgta      120
ggcatgatag aaatggatct ggccagcggc cgcacgctga ccgcctggcg cgccgatgaa      180
cgctttccca tgatgagcac ctttaaagta gtgctctgcg gcgcagtgct ggcgcgggtg      240
gatgccggtg acgaacagct ggagcgaaag atccactatc gccagcagga tctggtggac      300
tactcgccgg tcagcgaaaa acaccttgcc gacggcatga cggtcggcga actctgcgcc      360
gccgccatta ccatgagcga taacagcgcc gccaatctgc tactggccac cgtcggcggc      420
cccgcaggat tgactgcctt tttgcgccag atcggcgaca acgtcacccg ccttgaccgc      480
tgggaaacgg aactgaatga ggcgcttccc ggcgacgccc gcgacaccac taccccggcc      540
agcatggccg cgaccctgcg caagctgctg accagccagc gtctgagcgc ccgttcgcaa      600
cggcagctgc tgcagtggat ggtggacgat cgggtcgccg gaccgttgat ccgctccgtg      660
ctgccggcgg gctggtttat cgccgataag accggagctg gcgagcgggg tgcgcgcggg      720
attgtcgccc tgcttggccc gaataacaaa gcagagcgca ttgtggtgat ttatctgcgg      780
gataccccgg cgagcatggc cgagcgaaat cagcaaatcg ccgggatcgg cgcggcgctg      840
atcgagcact ggcaacgcta a                                                861
```

```
<210> SEQ ID NO 19
<211> LENGTH: 1149
<212> TYPE: DNA
<213> ORGANISM: Artificial Sequence
<220> FEATURE:
<223> OTHER INFORMATION: blaFOX-6

<400> SEQUENCE: 19
atgcaacaac ggcgtgcgtt cgcgctactg acgctgggta gcctgctgtt agccccttgt       60
acttatgcca gcggggaggc tccgttgacc gccgctgtgg acggcattat ccagccgatg      120
ctcaaggcgt atcggatccc ggggatggcg gtcgccgtac tgaaagatgg caaagcccac      180
tatttcaact atgggggttgc caaccgggag agtggccagc gcgtcagcga gcagaccctg      240
ttcgagattg gctcggtcag caagaccctg actgcgaccc tcggtgccta tgccgcggtc      300
aaggggggct ttgagctgga tgacaaggtg agccagcacg cccctggct caaaggttcc      360 gccttggatg gtgtgaccat ggccgagctt gccacctaca gtgcgggtgg tttgccgctg      420
cagttccccg atgaggtgga ttcgaatgac aagatgcgca cttactatcg gagctggtca      480
ccggtttatc cggcggggac ccatcgccag tattccaacc ccagcatcgg cctgtttggt      540
```

-continued

```
cacctggccg caaatagtct gggccagcca tttgagcaac tgatgagcca gaccctgctg       600
cccaagctgg gtttgcacca cacctatatc caggtaccgg agtcggctat ggtgaactat       660
gcctacggct attcgaagga agataagccc gtccgggtca ctccgggcgt gctggcagcc       720
gaggcttacg ggatcaagac cggctcggcg gatctgctga agtttgccga ggcaaacatg       780
gggtatcagg gagatgccgc ggtaaaaagc gcgatcgcgc tcacccacac cggtttctac       840
tcggtgggag acatgaccca gggactgggc tgggagagtt acgcctatcc ggtgaccgag       900
cagacattgc tggcgggtaa cgcaccggcg gtgagcttcc aggccaatcc ggttacgcgc       960
tttgcggtgc ccaaggcgat gggcgagcag cggctctata caagacgggc tcgactggcc      1020
ggctttggcg cctatgtggc gttcgtgccc gccagaggga tcgccatcgt catgctggcc      1080
aatcgcaact atcccatcga ggccagggtg aaggcggctc acgccatcct gagtcagttg      1140
gccgagtga                                                             1149

<210> SEQ ID NO 20
<211> LENGTH: 927
<212> TYPE: DNA
<213> ORGANISM: Artificial Sequence
<220> FEATURE:
<223> OTHER INFORMATION: blaPER-2

<400> SEQUENCE: 20
atgaatgtca tcacaaaatg tgttttcacc gcttctgctc tgctgatgct tggcttaagt        60
tcatttgtag tatcagccca atcccctttg ttaaaagagc agattgaaac catagtgacg       120
ggtaaaaagg ccactgtagg tgtagcagtg tggggggcctg acgatctgga acctttgttg       180
ctgaatccat ttgaaaagtt tccgatgcaa agtgtgttta aactgcattt agctatgtta       240
gttctgcatc aggtcgatca ggggaaactg gatttaaatc agtctgttac tgttaatcgt       300
gctgcagtat tacaaaatac ctggtcgcca atgatgaaag atcatcaggg cgatgaattt       360
actgttgcag tacagcagtt actgcagtat tcggtgtcac acagcgacaa tgtggcctgc       420
gatttgttat ttgaactggt gggcgggccg caagctttgc atgcttatat ccagtcttta       480
ggcgttaaag aagctgccgt ggtagcaaat gaagcgcaaa tgcatgcgga tgatcaggtg       540
caatatcaaa actggacgtc gatgaaagcc gcagcacaag ttctgcaaaa gtttgaacag       600
aaaaagcagt tgtctgaaac ctctcaggcc ttgttatgga atggatggt tgaaaccacc       660 acaggaccac agcggttaaa aggcttgtta cctgctggta ctatagtggc gcataaaacc       720
ggtacttcgg gcgtcagagc aggaaaaaact gcggcgacta atgatgcggg cgtcattatg       780
ttgcctgatg gacggccttt attggtggcg gtatttgtca aggattcggc tgaatcagaa       840
cgaaccaatg aagctattat tgcgcaggtt gcgcaagcgg cttatcagtt tgagctgaaa       900
aaactctctg cagtgagtcc ggattga                                         927

<210> SEQ ID NO 21
<211> LENGTH: 876
<212> TYPE: DNA
<213> ORGANISM: Artificial Sequence
<220> FEATURE:
<223> OTHER INFORMATION: blaCTX-M-15

<400> SEQUENCE: 21
atggttaaaa aatcactgcg ccagttcacg ctgatggcga cggcaaccgt cacgctgttg        60
ttaggaagtg tgccgctgta tgcgcaaacg gcggacgtac agcaaaaact tgccgaatta       120
gagcggcagt cgggaggcag actgggtgtg gcattgatta acacagcaga taattcgcaa       180
```

```
atactttatc gtgctgatga gcgctttgcg atgtgcagca ccagtaaagt gatggccgcg     240
gccgcggtgc tgaagaaaag tgaaagcgaa ccgaatctgt taaatcagcg agttgagatc     300
aaaaaatctg accttgttaa ctataatccg attgcggaaa agcacgtcaa tgggacgatg     360
tcactggctg agcttagcgc ggccgcgcta cagtacagcg ataacgtggc gatgaataag     420
ctgattgctc acgttggcgg cccggctagc gtcaccgcgt tcgcccgaca gctgggagac     480
gaaacgttcc gtctcgaccg taccgagccg acgttaaaca ccgccattcc gggcgatccg     540
cgtgatacca cttcacctcg ggcaatggcg caaactctgc ggaatctgac gctgggtaaa     600
gcattgggcg acagccaacg ggcgcagctg gtgacatgga tgaaaggcaa taccaccggt     660
gcagcgagca ttcaggctgg actgcctgct tcctgggttg tggggataa aaccggcagc      720 ggtggctatg gcaccaccaa cgatatcgcg gtgatctggc caaaagatcg tgcgccgctg     780
attctggtca cttacttcac ccagcctcaa cctaaggcag aaagccgtcg cgatgtatta     840
gcgtcggcgg ctaaaatcgt caccgacggt ttgtaa                               876

<210> SEQ ID NO 22
<211> LENGTH: 724
<212> TYPE: DNA
<213> ORGANISM: Artificial Sequence
<220> FEATURE:
<223> OTHER INFORMATION: stdA

<400> SEQUENCE: 22
atggaaagtt caggtgcttc gtttaacacc aggcgtttat tattcatacg aatcttttct      60
gaacgctttc attaataccc tcagagttgt tttcagcctt tgcaaaataa ttctcattca     120
cccaaaggac atattatcta tgcgtaataa aataatactt gccatggcgg ctgccggtat     180
gatgtatggt gcttctgtat ttgccgccga tactacaccc acagcaggcc cgttcggctc     240
aggtaaaatt cttttcactg gtaccatcac caactcaccc tgtgatatcg caccgggcga     300
cgatgcgatc accgttccgt ttggacagat ttcttaccgt aaactgaata ccgccaatgc     360
aaccacggac tcaaaaccgt tcaccattca tctgcagaac tgcgccttcg atccgaatga     420
aactacaata gccggctccg cagggaaaat gtctaaagta accgtctctt tcagtggcac     480
agcagatacc tcaggtaaag cttacgtcag caccggcagt gcccagcatg ttggtgtgca     540
gcttctgaaa ggtgacaaca cctcactgat tacacccaat accccgatgc cggatggcga     600
cgcccagcaa ctgcaggccg ggaataacga actcaacttc tttgcccgcc tgatagccct     660
gacagatgcc gcaactcctg gcgatgttaa cgcatccgtc acctacaccc tgaaatacct     720
gtga                                                                  724
```

METHOD AND DEVICE FOR DETECTION OF AMPICILLIN-RESISTANT NON-TYPHOIDAL *Salmonella*

CROSS-REFERENCE TO RELATED APPLICATION(S)

This application is the National Phase of PCT International Application No. PCT/CN2019/087834, filed on May 21, 2019, which claims priority under 35 U.S.C. 119(e) to U.S. Provisional Application No. 62/674,180, filed on May 21, 2018, all of which are hereby expressly incorporated by reference into the present application.

FIELD OF THE INVENTION

The present invention pertains to a method and a device for detection of an ampicillin-resistant non-typhoidal *Salmonella*.

BACKGROUND OF THE INVENTION

Non-typhoidal *Salmonella* (NTS) is one of the common enteropathogens in humans and animals worldwide and causes considerable morbidity and mortality in both children and general population [1]. NTS remains the leading cause of bacterial enteric infections in children and leads to bacteremia in 4.5%-15.1% of pediatric in-patients in Taiwan [2, 3]. A systemic review suggests that NTS are responsible for nearly 60% of bloodstream infections due to *Salmonella* and now more common than Typhoidal *Salmonella* causing enteric fever [4]. In addition, NTS infections constitute substantial socioeconomic burden because of increasing antimicrobial resistance (AMR) [5] and horizontal gene transfer through close food chains between humans and animals allows AMR in *Salmonella* to develop on a global scale [6].

In February 2017, World Health Organization announced *Salmonella* as one of the priority pathogens for development and research of new antibiotics due to concerns in its AMR [7]. The antibiotic resistance rates in NTS are drastically increasing worldwide and in Taiwan, and vary a lot worldwide even in different serotypes in the same country [5]. The ampicillin (AMP) resistance rates were 44% in unspecified serotypes of non-typhoidal *Salmonella*, 37.7% in *S. Braenderup*, and as high as 98% in *S. Choleraesuis* in Taiwan during 2007-2009 [5, 8]. The AMR rates of NTS in Taiwan are higher than those in other countries, with an overall resistance rate of 69% for any antibiotics, and increasing rates of 44% to 46.2% for AMP, 8% to 3.7% for ciprofloxacin (CIP), and 1.5% to 7.2% for ceftriaxone (CRO)/cefotaxime (CTX) from 2003 to 2016 [5, 9].

The increasing rates of AMR to the traditional first-line antibiotics (e.g. AMP, chloramphenicol, and trimethoprim-sulfamethoxazole), fluoroquinolone (e.g. CIP), extended-spectrum cephalosporin (e.g. CRO), and carbapenems (e.g. imipenem) have made the treatment of invasive *salmonellosis* troublesome [10, 11]. Previous reports in Taiwan warn of the development of CIP and CRO resistance, mainly from invasive *S. Choleraesuis* and *S. Schwarzengrund* [3, 12, 13]. Unfortunately, *S. Typhimurium, S. Choleraesuis,* and *S. Schwarzengrund* rank as the three most frequently isolated serotypes from human sources in Taiwan [14]. The emergence of CRO resistance in NTS is worrisome in Asia, particularly in Taiwan [10]. Resistance to extended-spectrum cephalosporins has occurred more often in non-typhoidal than in typhoidal *Salmonella* strains [11]. Furthermore, a *S. Typhimurium* strain resistant to carbapenem, which is the rescue drug for AMR to CIP and CRO, was reported with a $bla_{CMY\text{-}2}$-containing Tn6092 on a conjugate IncI1 plasmid and both OmpD/OmpC deficiency during ertapenem therapy. This is a warning of serious AMR in NTS due to restrained usage of available effective antibiotics for NTS.

Empirical use of antibiotics is an important cause of the above development of AMR in NTS. The increasing rates of AMR to the first-line antibiotics (e.g. ampicillin, chloramphenicol, and trimethoprim-sulfamethoxazole), the second-line antibiotics (e.g. fluoroquinolones and ceftriaxone), and the last choice carbapenems have made the treatment of invasive *salmonellosis* troublesome [10, 11]. Nowadays we mainly use approaches to reduce antibiotic consumption and AMR, including institutional antimicrobial stewardship programs, infection prevention, rational use of antimicrobials, regulation on over-the-counter availability of antibiotics, improving hand hygiene, and improving infection prevention and control [15]. However, more efficient approaches are required for combating AMR. According to the guideline of Clinical and Laboratory Standards Institute (CLSI), the currently used method for detecting bacterial antibiotic resistance from patients' samples takes at least 3 days. Overuse or incorrect use of empirical antibiotics in the first 3 days is one of the reasons why bacterial AMR increased dramatically in the past decades. So far, the traditional CLSI bacterial cultures with subsequent antimicrobial susceptibility tests or minimal inhibitory concentrations (MICs) remain the mainstream of diagnosing NTS infection. However, drawbacks of the CLSI methods included false negative results due to partial antibiotic treatment, low detection rates, and time consuming. Resistance to β-lactams remains a considerable concern in *Salmonella* because treatment is usually limited to β-lactams due to interference to cartilage formation by fluoroquinolone in children and fetus in pregnant women and avoidance of exacerbation in CIP and CRO [16]. Meanwhile, avoidance of using the third generation cephalosporin as the first-line antibiotic for treating salmonellosis can decelerate the worsening of resistance to these non-first-line antibiotics. If the diagnosis of NTS infection and the antimicrobial susceptibility test can be timely available e.g. within hours after patients' visit, doctors can precisely prescribe appropriate antibiotics for treatment and the problem of AMR can be controlled. Therefore, a rapid and accurate diagnostic tool for detection of *Salmonella* AMR is urgently warranted because subsequent precise use of effective antibiotics can ensue.

Currently documented genes associated with antibiotic resistance include the acquired AMR genes from plasmids and transposon in bacteria and point mutations within the genes located on bacterial chromosome [17]. So far, at least 1,223 genetic loci, including genes on plasmids/transposons or genetic mutations on truncal genomes, have been identified to be associated with AMP resistance in bacteria [18-20]. Theoretically, a multigene panel consisting of all the reported genetic loci or whole genome sequencing using NGS can almost accurately detect AMR in NTS. However, such a method is too time-consuming and costly to become a feasible rapid diagnostic tool for practical use. For rapid diagnosis, some rapid diagnostic tools are available to facilitate detection of multiple enteropathogens rather than a specific pathogen, but it is lacking of AMR testing. For the purpose of studying AMR genes, some microbial DNA quantitative PCR arrays are used for the detection and relative profiling of antibiotic resistance genes belonging to various antibiotics. However, such a tool is not designed for the diagnosis, prevention, or treatment of a disease or a pathogen. Therefore, a rapid accurate diagnostic tool is required for clinical use in diagnosing a specific bacterial pathogen and its AMR.

Recent high-throughput technologies have enabled genome-wide NGS studies from interpretation of human heritable diseases to approaches for addressing microbiological questions, focusing on three tasks: (1) identifying the species of an isolate, (2) testing its properties such as virulence and antibiotic resistance, and (3) monitoring the emergence and spread for bacterial pathogens [21]. NGS has become a feasible high-throughput technology implemented in genome sequencing of NTS for tackling NTS infections since 2012 [22]. In 2013, NGS was used to dissect the phylogenetic associations of multidrug-resistant *S. Typhimurium* DT104 and its antibiotic resistance genes through the course of an epidemic but failed to discover unreported genetic loci associated with antibiotic resistance [23]. So far NGS has rarely been thoroughly applied to identification of unreported genes associated with AMR in human NTS infection. Because *Salmonella enterica* is recognized as one of the most prevalent foodborne pathogens in poultry production and food safety, NGS tools provide a powerful approach for epidemiological trace-back assessment in which the population genome data can be used for assessing antibiotic susceptibility and detection of changes in resistance [24]. NGS was also used for discovery of unreported intergenic loci and genes involved in global stress, energy production, metabolism, membrane transport and pathogenicity after comparative transcriptomics of biocide-resistant mutants of *Salmonella enterica* [25]. With the introduction of the powerful NGS, the genomes of 25 *S. enterica* isolates from broiler chickens covering five serovars *Typhimurium, Enteritidis*, Hadar, Heidelberg and Kentucky were sequenced, and antibiotic resistance genes (CMY, aadA, ampC, florR, sull, sull, tetAB, and srtA) and class I integrons were identified in resistant isolates [26]. Such a comparative NGS analysis has been rarely done in human antibiotic-resistant NTS isolates for identification of candidate AMR genes and/or mutations responsible for clinical diagnosis of human NTS infection.

BRIEF SUMMARY OF THE INVENTION

The present invention is based on the unexpected finding that the presence of a combination of certain genes or their gene products can be used to detect ampicillin resistance of non-typhoidal *Salmonella* (NTS).

In an aspect, the present invention provides a method for determining whether a sample contains an ampicillin-resistant (AMP-R) NTS, comprising detecting, in the sample, the presence of a plurality of genes or gene products, wherein the plurality of genes or gene products comprise at least one combination of (i) a bla$_{TEM-1b}$ gene or its gene product, and a bla$_{OXA-1}$ gene or its gene product, and (ii) a bla$_{TEM-1b}$ gene or its gene product, and a bla$_{CARB-2}$ gene or its gene product, wherein the presence of said combination indicates the sample contains AMP-R NTS.

The plurality of genes or gene products may further comprise other biomarkers as desired. In some embodiments of the present invention, for example, such biomarkers can be selected from the group consisting of a bla$_{CMY-2}$ gene, an ampC gene, a Bla$_{CTX-M-9}$ gene, a bla$_{TEM-227}$ gene or their gene products and a combination thereof.

In one embodiment of the present invention, the plurality of genes or gene products comprise a combination of a bla$_{TEM-1b}$ gene, a bla$_{OXA-1}$ gene, and a bla$_{CARB-2}$ gene, or their gene products.

In one embodiment of the present invention, the plurality of genes or gene products comprise a bla$_{TEM-1b}$ gene or its gene product, a bla$_{OXA-1}$ gene or its gene product, and at least one gene selected from the group consisting of a bla$_{CMY-2}$ gene, an ampC gene, a bla$_{CTX-M-9}$ gene, and a bla$_{TEM-227}$ gene, or their gene products.

In another embodiment of the present invention, the plurality of genes or gene products comprise a bla$_{TEM-1b}$ gene or its gene product, a bla$_{CARB-2}$ gene or its gene product, and at least one gene selected from the group consisting of a bla$_{CMY-2}$ gene, an ampC gene, a bla$_{CTX-M-9}$ gene, and a bla$_{TEM-227}$ gene, or their gene products.

In still another embodiment of the present invention, the plurality of genes or gene products comprises a bla$_{TEM-1b}$ gene or its gene product, a bla$_{OXA-1}$ gene or its gene product, a bla$_{CARB-2}$ gene or its gene product and at least one gene selected from the group consisting of a bla$_{CMY-2}$ gene, an ampC gene, a bla$_{CTX-M-9}$ gene, and a bla$_{TEM-227}$ gene, or their gene products.

According to the present invention, the method may further comprise detecting a known universal gene for NTS, such as stdA (J Food Prot 2008; 71:1108-13) [27].

According to the present invention, the sample is a fecal sample or a body fluid sample (e.g., a blood sample or a urine sample), but is not limited thereto.

As could be appreciated, it is another object of the present invention to provide a detection device for determining whether a sample contains an AMP-R NTS, comprising detecting the presence of said plurality of genes or gene products.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1 illustrates a study design in NGS identification of NTS genes associated with ampicillin resistance and validation of one example set from the identified multigene panel in detection of ampicillin resistance in NTS isolates.

DETAILED DESCRIPTION OF THE INVENTION

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

In the context of the present invention, a "sample" is a sample which comprises at least one gene or its gene product from a bacterial microorganism. Examples for samples include, but not limited to, cells, tissue, body fluids, biopsy specimens, blood, urine, saliva, sputum, plasma, serum, cell culture supernatant, swab sample and others.

The sample is used interchangeably herein to refer to a sample obtained from any subject, particularly a vertebrate subject, and even more particularly a mammalian subject. Suitable vertebrate animals include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (snakes, frogs, lizards, etc.), and fish. A preferred subject is a primate (e.g., a human, ape, monkey, chimpanzee).

The term "gene" as used herein refers to any and all discrete coding regions of the eukaryotic or prokaryotic cell's genome, as well as associated non-coding and regulatory regions. The term "gene" is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

In accordance with the methods of the present invention, the presence and/or level of expression of the marker in a sample can be assessed, for example, by detecting the presence in the sample of: (a) a DNA or DNA fragment corresponding to the marker; (b) a protein or protein fragment corresponding to the marker (e.g. using a reagent, such as an antibody, an antibody derivative, or an antibody fragment, which binds specifically with the protein or protein fragment); (c) a transcribed polynucleotide (e.g. an mRNA or a cDNA), or fragment thereof, having at least a portion with which the marker is substantially homologous; (d) a metabolite which is produced directly (i.e., catalyzed) or indirectly by a protein corresponding to the marker; or (e) a transcribed polynucleotide or fragment thereof, wherein the polynucleotide anneals with the marker under stringent hybridization conditions.

The term "next generation sequencing (NGS)" as used herein refers to high-throughput sequencing technologies that parallelize the sequencing process, producing thousands or millions of sequences at once. Examples include, but not limited to, Massively Parallel Signature Sequencing (MPSS), Polony sequencing, 454 pyrosequencing, Illumina (Solexa) sequencing, SOLiD sequencing, Ion semiconductor sequencing, DNA nanoball sequencing, Helioscope™ single molecule sequencing, Single Molecule SMRT™ sequencing, Single Molecule real time (RNAP) sequencing, Nanopore DNA sequencing, Sequencing By Hybridization, Amplicon Sequencing, and GnuBio.

In some embodiments of the present invention, there is a NGS approach based on clustering bacterial clinical isolates by antibiotic-resistance phenotypes and sequencing the resultant pooled genomic DNA.

In some embodiments of the present invention, calculations of sequence similarity or sequence identity between sequences are performed as follows: to determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, usually at least 40%, more usually at least 50%, 60%, and even more usually at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e., conservative substitution) at the corresponding position in the second sequence, then the molecules are similar at that position.

The percent identity between the two sequences is a function of the number of identical sequences at individual positions, taking into account the number of gaps, and the length of each gap, which need to be introduced for optimal alignment of the two sequences. By contrast, the percent similarity between the two sequences is a function of the number of identical sequences at individual positions, taking into account the number of gaps, and the length of each gap, which need to be introduced for optimal alignment of the two sequences.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10).

In some embodiments of the present invention, a "polymerase chain reaction (PCR)" refers to an in vitro amplification reaction of polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. For example, in a conventional PCR using Taq DNA polymerase, a double stranded template polynucleotide can be denatured at a temperature>90° C., primers can be annealed at a temperature in the range 50-75° C., and primers can be extended at a temperature in the range 72-78°

C. In some embodiments, PCR comprises Reverse transcription PCR (RT-PCR), real-time PCR, nested PCR, quantitative PCR, multiplexed PCR, or the like.

The present disclosure is based, at least in part, on the finding that the presence of a combination of certain genes or their gene products, as identified herein below, can be used to detect ampicillin resistance of non-typhoidal *Salmonella* (NTS).

In view of the foregoing, the present invention provides a method for determining whether a sample contains an ampicillin-resistant (AMP-R) NTS, comprising detecting, in the sample, the presence of a plurality of genes or gene products, wherein the plurality of genes or gene products comprises at least one combination of (i) a $bla_{TEM-1b}$ gene or its gene product, and a $bla_{OXA-1}$ gene or its gene product, and (ii) a $bla_{TEM-1b}$ gene or its gene product, and a $bla_{CARB-2}$ gene or its gene product, wherein the presence of said combination indicates the sample contains AMP-R NTS.

Regarding the method for determining whether a sample contains an AMP-R NTS, the presence of a plurality of genes or gene products is determined using PCR of NGS, according to examples provided below. However, as could be appreciated, the present method is not limited to the methods described below; rather, the scope of the claimed invention encompasses the use of other equivalent methods for determining the presence of level of the plurality of genes or gene products.

In some embodiments, in addition to the at least one combination of (i) a $bla_{TEM-1b}$ gene or its gene product, and a $bla_{OXA-1}$ gene or its gene product, and (ii) a $bla_{TEM-1b}$ gene or its gene product, and a $bla_{CARB-2}$ gene or its gene product, the plurality of genes or gene products further comprise at least one of a $bla_{CMY-2}$ gene, an ampC gene, a $bla_{CTX-M-9}$ gene, a $bla_{TEM-227}$ gene or their gene products.

According to certain optional embodiments, the plurality of genes or gene products comprise a $bla_{TEM-1b}$ gene or its gene product, and a $bla_{OXA-1}$ gene or its gene product. In some embodiments, the plurality of genes or gene products comprise a $bla_{TEM-1b}$ gene or its gene product, and a $bla_{CARB-2}$ gene or its gene product. In some embodiments, the plurality of genes or gene products comprise a $bla_{TEM-1b}$ gene or its gene product, a $bla_{OXA-1}$ gene or its gene product, and a $bla_{CARB-2}$ gene or its gene product.

In some embodiments of the present invention, the plurality of genes or gene products comprise a $bla_{TEM-1b}$ gene or its gene product, a $bla_{OXA-1}$ gene or its gene product, and at least one of a $bla_{CMY-2}$ gene, an ampC gene, a $bla_{CTX-M-9}$ gene, a $bla_{TEM-227}$ gene or their gene products. In one embodiment, the plurality of genes or gene products comprise a $bla_{TEM-1b}$ gene or its gene product, a $bla_{OXA-1}$ gene or its gene product, and a $bla_{CMY-2}$ gene or its gene product. In one embodiment, the plurality of genes or gene products comprise a $bla_{TEM-1b}$ gene or its gene product, a $bla_{OXA-1}$ gene or its gene product, and an ampC gene or its gene product. In one embodiment, the plurality of genes or gene products comprise a $bla_{TEM-1b}$ gene or its gene product, a $bla_{OXA-1}$ gene or its gene product, and a $bla_{CTX-M-9}$ gene or its gene product. In one embodiment, the plurality of genes or gene products comprise a $bla_{TEM-1b}$ gene or its gene product, a $bla_{OXA-1}$ gene or its gene product, and a $bla_{TEM-227}$ gene or its gene product.

In some embodiments of the present invention, the plurality of genes or gene products comprise a $bla_{TEM-1b}$ gene or its gene product, and a $bla_{CARB-2}$ gene or its gene product, and at least one of a $bla_{CMY-2}$ gene, an ampC gene, a $bla_{CTX-M-9}$ gene, a $bla_{TEM-227}$ gene or their gene products. In one embodiment, the plurality of genes or gene products comprise a $bla_{TEM-1b}$ gene or its gene product, and a $bla_{CARB-2}$ gene or its gene product, and a $bla_{CMY-2}$ gene or its gene product. In one embodiment, the plurality of genes or gene products comprise a $bla_{TEM-1b}$ gene or its gene product, and a $bla_{CARB-2}$ gene or its gene product, and an ampC gene or its gene product. In one embodiment, the plurality of genes or gene products comprise a $bla_{TEM-1b}$ gene or its gene product, and a $bla_{CARB-2}$ gene or its gene product, and a $bla_{CTX-M-9}$ gene or its gene product. In one embodiment, the plurality of genes or gene products comprise a $bla_{TEM-1b}$ gene or its gene product, and a $bla_{CARB-2}$ gene or its gene product, and a $bla_{TEM-227}$ gene or its gene product.

In some embodiments of the present invention, the plurality of genes or gene products comprise a $bla_{TEM-1b}$ gene or its gene product, a $bla_{OXA-1}$ gene or its gene product, a $bla_{CARB-2}$ gene or its gene product, and at least one of a $bla_{CMY-2}$ gene, an ampC gene, a $bla_{CTX-M-9}$ gene, a $bla_{TEM-227}$ gene or their gene products. In one embodiment, the plurality of genes or gene products comprise a $bla_{TEM-1b}$ gene or its gene product, a $bla_{OXA-1}$ gene or its gene product, a $bla_{CARB-2}$ gene or its gene product, and a $bla_{CMY-2}$ gene or its gene product. In one embodiment, the plurality of genes or gene products comprise a $bla_{TEM-1b}$ gene or its gene product, a $bla_{OXA-1}$ gene or its gene product, and a $bla_{CARB-2}$ gene or its gene product, and an ampC gene or its gene product. In one embodiment, the plurality of genes or gene products comprise a $bla_{TEM-1b}$ gene or its gene product, a $bla_{OXA-1}$ gene or its gene product, a $bla_{CARB-2}$ gene or its gene product, and a $bla_{CTX-M-9}$ gene or its gene product. In one embodiment, the plurality of genes or gene products comprise a $bla_{TEM-1b}$ gene or its gene product, a $bla_{OXA-1}$ gene or its gene product, a $bla_{CARB-2}$ gene or its gene product, and a $bla_{TEM-227}$ gene or its gene product.

In the embodiments of the present invention where the presence of the plurality of genes or gene products is determined, the assessment may be made based on the presence or absence of said plurality of genes or gene products.

In several embodiments of the present invention, a universal gene is applied to confirm whether the test sample comprises a NTS.

According to various embodiments of the present invention, the universal gene is stdA.

Alternatively, the scope of the claimed invention encompasses the use of other equivalent universal gene for determining whether the test sample comprises a NTS.

According to various embodiments of the present invention, the sample is derived from a fecal sample or a body fluid sample.

As could be appreciated, the plurality of genes or gene products identified in the present invention could be used to prepare detection tools for assessing whether a sample has an AMP-R NTS.

For example, the detection device may comprise materials that could be used to determine the presence of the plurality of genes or gene products disclosed herein, such as $bla_{TEM-1b}$, $bla_{OXA-1}$, $bla_{CARB-2}$, $bla_{CMY-2}$, ampC, $bla_{CTX-M-9}$, $bla_{TEM-227}$, and stdA, or their gene products.

The present invention is further illustrated by the following Examples, which are provided for the purpose of demonstration rather than limitation.

EXAMPLES

Materials and Methods

1. Study Design

The design of this study is depicted in FIG. 1. This study was conducted using NGS in NTS clinical isolates to identify a representative panel of genes associated with ampicillin resistance in a minimum number that can be applied for accurate detection of NTS and its resistance to ampicillin.

After obtaining the original 53 NGS clinical isolates from different hospitals in various geographical regions, we conducted antimicrobial susceptibility tests and extracted DNA for whole genome sequencing at the same time. On the one hand, we first attempted to find out the most important acquired genes associated with ampicillin resistance in NTS by aligning the sequences of our isolates with antimicrobial resistance gene sequences from databases. After identification of a representative multigene panel for detection of ampicillin resistance and universal presence of the stdA gene responsible for fimbria adhesion of NTS, we further validated one example set of the identified 4 genes plus stdA using PCR technique in a total of 169 NTS isolates.

2. Bacterial Strains and Culture Conditions

A total of 169 NTS clinical isolates were used in this study, including 49 NTS isolates collected from pediatric patients at Taipei Medical University Shuang Ho Hospital (TMU-SHH) from 2011 to 2015, and 120 NTS isolates from the Taiwan Surveillance of Antibiotic Resistance (TSAR) at National Health Research Institutes (NHRI) during 2010-2016. TSAR is regularly collecting bacterial samples with AMR from different hospitals in northern, central, southern, and eastern Taiwan in collaboration with Taiwan Centers for Disease Control (CDC). The 169 NTS isolates consist of 108 ampicillin-resistant (AMP-R) isolates (63%) and 61 ampicillin-susceptible (AMP-S) isolates (36%). A total of 53 NTS isolates from TMU-SHH and TSAR at NHRI (11 AMP-S isolates and 42 AMP-R isolates) were used for the first setting in the NGS study (Table 1), whereas these 53 NTS isolates together with additional 116 NTS isolates composing a total of 169 NTS isolates from the above two resources were used for the second setting in the PCR study (Table 2) for validation of the NGS results. All bacterial isolates were frozen at −80° C. For maintenance, all bacteria were cultured onto Luria-Bertani (LB) agar (Sigma-Aldrich, St. Louis, MO) at 37° C. for 18 hours.

TABLE 1

ID with sources, serotypes, ampicillin resistance (AMP-R), the 7 NGS-identified AMP-R genes, and the universal stdA gene in the 53 NTS isolates from TMU-SHH and TSAR at NHRI for the NGS study (Δ = correct prediction; R = Resistant to ampicillin; S = Susceptible to ampicillin; 1 = detected; 0 = not detected).

| No. | ID | Serotype | Method | AMP-R | $bla_{TEM-1b}$ | $bla_{OXA-1}$ | $bla_{CARB-2}$ | $bla_{TEM-227}$ | $bla_{CMY-2}$ | ampC | $bla_{CTX-M-9}$ | stdA |
|---|---|---|---|---|---|---|---|---|---|---|---|---|
| 1 | SH-A1 | Enteritidis | NGS | S | 0Δ | 0Δ | 0Δ | 0Δ | 0Δ | 0Δ | 0Δ | 1Δ |
| 2 | SH-B2 | Enteritidis | NGS | R | 1Δ | 0 | 0 | 0 | 1Δ | 1Δ | 0 | 1Δ |
| 3 | SH-B5 | Enteritidis | NGS | R | 1Δ | 0 | 0 | 0 | 0 | 0 | 0 | 1Δ |
| 4 | SH-C2 | Newport | NGS | S | 0Δ | 0Δ | 0Δ | 0Δ | 0Δ | 0Δ | 0Δ | 1Δ |
| 5 | SH-C3 | Enteritidis | NGS | S | 0Δ | 0Δ | 0Δ | 0Δ | 0Δ | 0Δ | 0Δ | 1Δ |
| 6 | SH-C4 | Typhimurium | NGS | R | 0 | 0 | 0 | 0 | 0 | 0 | 0 | 1Δ |
| 7 | SH-D2 | Enteritidis | NGS | S | 0Δ | 0Δ | 0Δ | 0Δ | 0Δ | 0Δ | 0Δ | 1Δ |
| 8 | SH-D4 | Enteritidis | NGS | S | 0Δ | 0Δ | 0Δ | 0Δ | 0Δ | 0Δ | 0Δ | 1Δ |
| 9 | SH-D5 | Typhimurium | NGS | S | 0Δ | 0Δ | 0Δ | 0Δ | 0Δ | 0Δ | 0Δ | 1Δ |
| 10 | SH-E1 | Unknown | NGS | R | 0 | 0 | 0 | 0 | 0 | 0 | 0 | 1Δ |
| 11 | SH-E2 | Virchow | NGS | S | 0Δ | 0Δ | 0Δ | 0Δ | 0Δ | 0Δ | 0Δ | 1Δ |
| 12 | SH-E3 | Newport | NGS | S | 0Δ | 0Δ | 0Δ | 0Δ | 0Δ | 0Δ | 0Δ | 1Δ |
| 13 | SH-F4 | Typhimurium | NGS | R | 0 | 0 | 0 | 0 | 0 | 0 | 0 | 1Δ |
| 14 | SH-F5 | Enteritidis | NGS | R | 1Δ | 0 | 0 | 0 | 0 | 0 | 0 | 1Δ |
| 15 | SH-G1 | Stanley | NGS | S | 0Δ | 0Δ | 0Δ | 0Δ | 0Δ | 0Δ | 0Δ | 1Δ |
| 16 | SH-G2 | Typhimurium | NGS | R | 0 | 0 | 0 | 0 | 1Δ | 1Δ | 0 | 1Δ |
| 17 | SH-G3 | Enteritidis | NGS | R | 1Δ | 0 | 0 | 0 | 0 | 0 | 0 | 1Δ |
| 18 | SH-G5 | Albany | NGS | R | 0 | 0 | 1Δ | 0 | 0 | 0 | 0 | 1Δ |
| 19 | SH-H3 | Derby | NGS | S | 0Δ | 0Δ | 0Δ | 0Δ | 0Δ | 0Δ | 0Δ | 1Δ |
| 20 | SH-H4 | Newport | NGS | R | 1Δ | 0 | 0 | 0 | 0 | 0 | 0 | 1Δ |
| 21 | SH-12 | Amsterdam | NGS | S | 0Δ | 0Δ | 0Δ | 0Δ | 0Δ | 0Δ | 0Δ | 1Δ |
| 22 | TSAR-C1 | Schwarzengrund | NGS | R | 1Δ | 0 | 0 | 0 | 0 | 0 | 0 | 1Δ |
| 23 | TSAR-C2 | Schwarzengrund | NGS | R | 0 | 0 | 0 | 0 | 0 | 0 | 0 | 1Δ |
| 24 | TSAR-C3 | Schwarzengrund | NGS | R | 1Δ | 0 | 0 | 0 | 0 | 0 | 0 | 1Δ |
| 25 | TSAR-C4 | Typhimurium | NGS | R | 0 | 1Δ | 0 | 0 | 0 | 0 | 0 | 1Δ |
| 26 | TSAR-C5 | Choleraesuis | NGS | R | 0 | 0 | 0 | 0 | 0 | 0 | 0 | 1Δ |
| 27 | TSAR-C6 | Typhimurium | NGS | R | 1Δ | 1Δ | 0 | 0 | 0 | 0 | 0 | 1Δ |
| 28 | TSAR-C7 | Typhimurium | NGS | R | 0 | 1Δ | 0 | 0 | 0 | 0 | 0 | 1Δ |
| 29 | TSAR-C10 | Enteritidis | NGS | R | 1Δ | 0 | 0 | 0 | 0 | 0 | 0 | 1Δ |
| 30 | TSAR-C13 | Stanley | NGS | R | 1Δ | 0 | 0 | 0 | 0 | 0 | 0 | 1Δ |
| 31 | TSAR-C16 | Typhimurium | NGS | R | 1Δ | 0 | 0 | 0 | 0 | 0 | 0 | 1Δ |
| 32 | TSAR-C19 | Stanley | NGS | R | 1Δ | 0 | 0 | 0 | 0 | 0 | 0 | 1Δ |
| 33 | TSAR-E5 | Choleraesuis | NGS | R | 1Δ | 0 | 0 | 0 | 0 | 0 | 0 | 1Δ |
| 34 | TSAR-E9 | Choleraesuis | NGS | R | 0 | 0 | 0 | 1Δ | 0 | 0 | 0 | 1Δ |
| 35 | TSAR-E10 | Typhimurium | NGS | R | 1Δ | 0 | 0 | 0 | 0 | 0 | 0 | 1Δ |
| 36 | TSAR-E16 | Virchow | NGS | R | 0 | 0 | 0 | 0 | 0 | 0 | 0 | 1Δ |
| 37 | TSAR-E18 | Meleagridis | NGS | R | 0 | 0 | 0 | 0 | 0 | 0 | 0 | 1Δ |
| 38 | TSAR-E19 | Newport | NGS | R | 1Δ | 0 | 0 | 0 | 0 | 0 | 0 | 1Δ |
| 39 | TSAR-E20 | Typhimurium | NGS | R | 1Δ | 0 | 0 | 0 | 0 | 0 | 0 | 1Δ |
| 40 | TSAR-N5 | Typhimurium | NGS | R | 0 | 1Δ | 0 | 0 | 0 | 0 | 0 | 1Δ |
| 41 | TSAR-N8 | Typhimurium | NGS | R | 0 | 1Δ | 0 | 0 | 0 | 0 | 0 | 1Δ |
| 42 | TSAR-N9 | Montevideo | NGS | R | 1Δ | 0 | 0 | 0 | 0 | 0 | 1 | 1Δ |
| 43 | TSAR-N15 | Schwarzengrund | NGS | R | 1Δ | 0 | 0 | 0 | 0 | 0 | 0 | 1Δ |
| 44 | TSAR-N16 | Agona | NGS | R | 0 | 1Δ | 0 | 0 | 0 | 0 | 0 | 1Δ |
| 45 | TSAR-N19 | Enteritidis | NGS | R | 1Δ | 0 | 0 | 0 | 0 | 0 | 0 | 1Δ |
| 46 | TSAR-S13 | Albany | NGS | R | 0 | 0 | 1Δ | 0 | 0 | 0 | 0 | 1Δ |

TABLE 1-continued

ID with sources, serotypes, ampicillin resistance (AMP-R), the 7 NGS-identified AMP-R genes, and the universal stdA gene in the 53 NTS isolates from TMU-SHH and TSAR at NHRI for the NGS study (Δ = correct prediction; R = Resistant to ampicillin; S = Susceptible to ampicillin; 1 = detected; 0 = not detected).

| No. | ID | Serotype | Method | AMP-R | $bla_{TEM-1b}$ | $bla_{OXA-1}$ | $bla_{CARB-2}$ | $bla_{TEM-227}$ | $bla_{CMY-2}$ | ampC | $bla_{CTX-M-9}$ | stdA |
|---|---|---|---|---|---|---|---|---|---|---|---|---|
| 47 | TSAR-S14 | Typhimurium | NGS | R | 0 | 0 | 1Δ | 0 | 0 | 0 | 0 | 1Δ |
| 48 | TSAR-S15 | Enteritidis | NGS | R | 0 | 0 | 0 | 0 | 0 | 0 | 0 | 1Δ |
| 49 | TSAR-S16 | Agona | NGS | R | 0 | 0 | 1Δ | 0 | 0 | 0 | 0 | 1Δ |
| 50 | TSAR-S17 | Newport | NGS | R | 1Δ | 0 | 0 | 0 | 0 | 0 | 0 | 1Δ |
| 51 | TSAR-S18 | Newport | NGS | R | 1Δ | 0 | 0 | 0 | 0 | 0 | 0 | 1Δ |
| 52 | TSAR-S19 | Agona | NGS | R | 0 | 0 | 0 | 0 | 0 | 0 | 0 | 1Δ |
| 53 | TSAR-S20 | Livingstone | NGS | R | 1Δ | 0 | 0 | 0 | 0 | 0 | 0 | 1Δ |

TABLE 2

ID with sources, ampicillin resistance (AMP-R), the selected 4 NGS-identified AMP-R genes, and the universal stdA gene in the 169 NTS isolates from TMU-SHH and TSAR at NHRI for the PCR study (Δ = correct prediction; R = Resistant to ampicillin; S = Susceptible to ampicillin; 1 = detected; 0 = not detected).

| No. | ID | Method | AMP-R | $bla_{TEM-1b}$ | $bla_{CARB-2}$ | $bla_{CMY-2}$ | ampC | stdA |
|---|---|---|---|---|---|---|---|---|
| 1 | SH-A1 | PCR | S | 0Δ | 0Δ | 0Δ | 0Δ | 1Δ |
| 2 | SH-B2 | PCR | R | 1Δ | 0 | 1Δ | 1Δ | 1Δ |
| 3 | SH-B5 | PCR | R | 1Δ | 0 | 0 | 0 | 1Δ |
| 4 | SH-C2 | PCR | S | 0Δ | 0Δ | 0Δ | 0Δ | 1Δ |
| 5 | SH-C3 | PCR | S | 0Δ | 0Δ | 0Δ | 0Δ | 1Δ |
| 6 | SH-C4 | PCR | R | 1Δ | 0 | 0 | 0 | 1Δ |
| 7 | SH-D2 | PCR | S | 0Δ | 0Δ | 0Δ | 0Δ | 1Δ |
| 8 | SH-D4 | PCR | S | 0Δ | 0Δ | 0Δ | 0Δ | 1Δ |
| 9 | SH-D5 | PCR | S | 0Δ | 0Δ | 0Δ | 0Δ | 1Δ |
| 10 | SH-E1 | PCR | R | 0 | 0 | 0 | 0 | 1Δ |
| 11 | SH-E2 | PCR | S | 0Δ | 0Δ | 0Δ | 0Δ | 1Δ |
| 12 | SH-E3 | PCR | S | 0Δ | 0Δ | 0Δ | 0Δ | 1Δ |
| 13 | SH-F4 | PCR | R | 0 | 0 | 0 | 0 | 1Δ |
| 14 | SH-F5 | PCR | R | 1Δ | 0 | 0 | 0 | 1Δ |
| 15 | SH-G1 | PCR | S | 0Δ | 0Δ | 0Δ | 0Δ | 1Δ |
| 16 | SH-G2 | PCR | R | 0 | 0 | 1Δ | 1Δ | 1Δ |
| 17 | SH-G3 | PCR | R | 1Δ | 0 | 0 | 0 | 1Δ |
| 18 | SH-G5 | PCR | R | 0 | 1Δ | 0 | 0 | 1Δ |
| 19 | SH-H3 | PCR | S | 0Δ | 0Δ | 0Δ | 0Δ | 1Δ |
| 20 | SH-H4 | PCR | R | 1Δ | 0 | 0 | 0 | 1Δ |
| 21 | SH-12 | PCR | S | 0Δ | 0Δ | 0Δ | 0Δ | 1Δ |
| 22 | TSAR-C1 | PCR | R | 0 | 0 | 0 | 0 | 1Δ |
| 23 | TSAR-C2 | PCR | R | 0 | 0 | 0 | 0 | 1Δ |
| 24 | TSAR-C3 | PCR | R | 0 | 0 | 0 | 0 | 1Δ |
| 25 | TSAR-C4 | PCR | R | 0 | 0 | 0 | 0 | 1Δ |
| 26 | TSAR-C5 | PCR | R | 0 | 0 | 0 | 0 | 1Δ |
| 27 | TSAR-C6 | PCR | R | 0 | 0 | 0 | 0 | 1Δ |
| 28 | TSAR-C7 | PCR | R | 0 | 0 | 0 | 0 | 1Δ |
| 29 | TSAR-C10 | PCR | R | 0 | 0 | 0 | 0 | 1Δ |
| 30 | TSAR-C13 | PCR | R | 0 | 0 | 0 | 0 | 1Δ |
| 31 | TSAR-C16 | PCR | R | 0 | 0 | 0 | 0 | 1Δ |
| 32 | TSAR-C19 | PCR | R | 0 | 0 | 0 | 0 | 1Δ |
| 33 | TSAR-E5 | PCR | R | 0 | 0 | 0 | 0 | 1Δ |
| 34 | TSAR-E9 | PCR | R | 0 | 0 | 0 | 0 | 1Δ |
| 35 | TSAR-E10 | PCR | R | 0 | 0 | 0 | 0 | 1Δ |
| 36 | TSAR-E16 | PCR | R | 0 | 0 | 0 | 0 | 1Δ |
| 37 | TSAR-E18 | PCR | R | 0 | 0 | 0 | 0 | 1Δ |
| 38 | TSAR-E19 | PCR | R | 0 | 0 | 0 | 0 | 1Δ |
| 39 | TSAR-E20 | PCR | R | 0 | 0 | 0 | 0 | 1Δ |
| 40 | TSAR-N5 | PCR | R | 0 | 0 | 0 | 0 | 1Δ |
| 41 | TSAR-N8 | PCR | R | 0 | 0 | 0 | 0 | 1Δ |
| 42 | TSAR-N9 | PCR | R | 0 | 0 | 0 | 0 | 1Δ |
| 43 | TSAR-N15 | PCR | R | 0 | 0 | 0 | 0 | 1Δ |
| 44 | TSAR-N16 | PCR | R | 0 | 0 | 0 | 0 | 1Δ |
| 45 | TSAR-N19 | PCR | R | 0 | 0 | 0 | 0 | 1Δ |
| 46 | TSAR-S13 | PCR | R | 0 | 0 | 0 | 0 | 1Δ |
| 47 | TSAR-S1Δ | PCR | R | 0 | 0 | 0 | 0 | 1Δ |
| 48 | TSAR-S15 | PCR | R | 0 | 0 | 0 | 0 | 1Δ |
| 49 | TSAR-S16 | PCR | R | 0 | 0 | 0 | 0 | 1Δ |
| 50 | TSAR-S17 | PCR | R | 0 | 0 | 0 | 0 | 1Δ |
| 51 | TSAR-S18 | PCR | R | 0 | 0 | 0 | 0 | 1Δ |
| 52 | TSAR-S19 | PCR | R | 0 | 0 | 0 | 0 | 1Δ |
| 53 | TSAR-S20 | PCR | R | 0 | 0 | 0 | 0 | 1Δ |

TABLE 2-continued

ID with sources, ampicillin resistance (AMP-R), the selected 4 NGS-identified AMP-R genes,
and the universal stdA gene in the 169 NTS isolates from TMU-SHH and TSAR at NHRI for the
PCR study (Δ = correct prediction; R = Resistant to ampicillin; S = Susceptible to ampicillin;
1 = detected; 0 = not detected).

| No. | ID | Method | AMP-R | bla$_{TEM-1b}$ | bla$_{CARB-2}$ | bla$_{CMY-2}$ | ampC | stdA |
|---|---|---|---|---|---|---|---|---|
| 54 | SH-A2 | PCR | R | 1Δ | 0 | 0 | 0 | 1Δ |
| 55 | SH-A3 | PCR | R | 0 | 1Δ | 0 | 0 | 1Δ |
| 56 | SH-A5 | PCR | S | 0Δ | 0Δ | 0Δ | 0Δ | 1Δ |
| 57 | SH-A6 | PCR | S | 0Δ | 0Δ | 0Δ | 0Δ | 1Δ |
| 58 | SH-B1 | PCR | R | 1Δ | 0 | 0 | 0 | 1Δ |
| 59 | SH-B3 | PCR | R | 1Δ | 0 | 0 | 0 | 1Δ |
| 60 | SH-B4 | PCR | R | 1Δ | 0 | 0 | 0 | 1Δ |
| 61 | SH-B6 | PCR | R | 1Δ | 0 | 0 | 0 | 1Δ |
| 62 | SH-C1 | PCR | R | 1Δ | 0 | 0 | 0 | 1Δ |
| 63 | SH-C5 | PCR | S | 0Δ | 0Δ | 0Δ | 0Δ | 1Δ |
| 64 | SH-C6 | PCR | R | 1Δ | 0 | 0 | 0 | 1Δ |
| 65 | SH-D1 | PCR | R | 1Δ | 0 | 0 | 0 | 1Δ |
| 66 | SH-D3 | PCR | S | 1 | 0Δ | 0Δ | 0Δ | 1Δ |
| 67 | SH-D6 | PCR | S | 0Δ | 0Δ | 0Δ | 0Δ | 1Δ |
| 68 | SH-E4 | PCR | S | 0Δ | 0Δ | 0Δ | 0Δ | 1Δ |
| 69 | SH-E5 | PCR | R | 1Δ | 0 | 1Δ | 0 | 1Δ |
| 70 | SH-E6 | PCR | R | 1Δ | 0 | 0 | 0 | 1Δ |
| 71 | SH-F1 | PCR | S | 1 | 0Δ | 0Δ | 0Δ | 1Δ |
| 72 | SH-F2 | PCR | R | 1Δ | 0 | 0 | 0 | 1Δ |
| 73 | SH-F3 | PCR | S | 0Δ | 0Δ | 0Δ | 0Δ | 1Δ |
| 74 | SH-G4 | PCR | R | 1Δ | 0 | 0 | 0 | 1Δ |
| 75 | SH-G6 | PCR | R | 1Δ | 0 | 0 | 0 | 1Δ |
| 76 | SH-H1 | PCR | R | 1Δ | 0 | 0 | 0 | 1Δ |
| 77 | SH-H2 | PCR | S | 0Δ | 0Δ | 0Δ | 0Δ | 1Δ |
| 78 | SH-H5 | PCR | S | 0Δ | 0Δ | 0Δ | 0Δ | 1Δ |
| 79 | SH-H6 | PCR | R | 1Δ | 0 | 0 | 0 | 1Δ |
| 80 | SH-14 | PCR | R | 1Δ | 0 | 0 | 0 | 1Δ |
| 81 | SH-15 | PCR | R | 1Δ | 0 | 0 | 0 | 1Δ |
| 82 | TSAR-C8 | PCR | R | 0 | 1Δ | 0 | 0 | 1Δ |
| 83 | TSAR-C9 | PCR | R | 0 | 1Δ | 0 | 0 | 1Δ |
| 84 | TSAR-C11 | PCR | R | 0 | 1Δ | 0 | 1Δ | 1Δ |
| 85 | TSAR-C12 | PCR | R | 0 | 1Δ | 0 | 0 | 1Δ |
| 86 | TSAR-C14 | PCR | R | 0 | 0 | 1Δ | 1Δ | 1Δ |
| 87 | TSAR-C15 | PCR | R | 0 | 1Δ | 0 | 0 | 1Δ |
| 88 | TSAR-C17 | PCR | R | 0 | 1Δ | 0 | 0 | 1Δ |
| 89 | TSAR-C18 | PCR | R | 0 | 1Δ | 0 | 0 | 1Δ |
| 90 | TSAR-C20 | PCR | R | 0 | 1Δ | 0 | 0 | 1Δ |
| 91 | TSAR-C21 | PCR | S | 0Δ | 0Δ | 0Δ | 0Δ | 1Δ |
| 92 | TSAR-C22 | PCR | S | 0Δ | 0Δ | 0Δ | 0Δ | 1Δ |
| 93 | TSAR-C23 | PCR | S | 0Δ | 0Δ | 0Δ | 0Δ | 1Δ |
| 94 | TSAR-C24 | PCR | S | 0Δ | 0Δ | 0Δ | 0Δ | 1Δ |
| 95 | TSAR-C25 | PCR | S | 0Δ | 0Δ | 0Δ | 0Δ | 1Δ |
| 96 | TSAR-C26 | PCR | S | 0Δ | 0Δ | 0Δ | 0Δ | 1Δ |
| 97 | TSAR-C27 | PCR | S | 0Δ | 0Δ | 0Δ | 0Δ | 1Δ |
| 98 | TSAR-C28 | PCR | S | 0Δ | 0Δ | 0Δ | 0Δ | 1Δ |
| 99 | TSAR-C29 | PCR | S | 0Δ | 0Δ | 0Δ | 0Δ | 1Δ |
| 100 | TSAR-C30 | PCR | S | 0Δ | 0Δ | 0Δ | 0Δ | 1Δ |
| 101 | TSAR-E1 | PCR | R | 1Δ | 0 | 0 | 0 | 1Δ |
| 102 | TSAR-E2 | PCR | R | 1Δ | 0 | 0 | 0 | 1Δ |
| 103 | TSAR-E3 | PCR | R | 1Δ | 0 | 0 | 0 | 1Δ |
| 104 | TSAR-E4 | PCR | R | 1Δ | 0 | 0 | 0 | 1Δ |
| 105 | TSAR-E6 | PCR | R | 1Δ | 0 | 0 | 0 | 1Δ |
| 106 | TSAR-E7 | PCR | R | 1Δ | 0 | 0 | 0 | 1Δ |
| 107 | TSAR-E8 | PCR | R | 1Δ | 0 | 0 | 0 | 1Δ |
| 108 | TSAR-E11 | PCR | R | 1Δ | 0 | 0 | 0 | 1Δ |
| 109 | TSAR-E12 | PCR | R | 1Δ | 0 | 0 | 0 | 1Δ |
| 110 | TSAR-E13 | PCR | R | 0 | 1Δ | 0 | 0 | 1Δ |
| 111 | TSAR-E14 | PCR | R | 0 | 1Δ | 0 | 0 | 1Δ |
| 112 | TSAR-E15 | PCR | R | 0 | 1Δ | 0 | 0 | 1Δ |
| 113 | TSAR-E17 | PCR | R | 0 | 1Δ | 0 | 0 | 1Δ |
| 114 | TSAR-E21 | PCR | S | 0Δ | 0Δ | 0Δ | 0Δ | 1Δ |
| 115 | TSAR-E22 | PCR | S | 0Δ | 0Δ | 0Δ | 0Δ | 1Δ |
| 116 | TSAR-E23 | PCR | S | 0Δ | 0Δ | 0Δ | 0Δ | 1Δ |
| 117 | TSAR-E24 | PCR | S | 0Δ | 0Δ | 0Δ | 0Δ | 1Δ |
| 118 | TSAR-E25 | PCR | S | 0Δ | 0Δ | 0Δ | 0Δ | 1Δ |
| 119 | TSAR-E26 | PCR | S | 0Δ | 0Δ | 0Δ | 0Δ | 1Δ |
| 120 | TSAR-E27 | PCR | S | 0Δ | 0Δ | 0Δ | 0Δ | 1Δ |
| 121 | TSAR-E28 | PCR | S | 0Δ | 0Δ | 0Δ | 0Δ | 1Δ |
| 122 | TSAR-E29 | PCR | S | 0Δ | 0Δ | 0Δ | 0Δ | 1Δ |
| 123 | TSAR-E30 | PCR | S | 0Δ | 0Δ | 0Δ | 0Δ | 1Δ |
| 124 | TSAR-N1 | PCR | R | 1Δ | 0 | 0 | 0 | 1Δ |
| 125 | TSAR-N2 | PCR | R | 1Δ | 0 | 0 | 0 | 1Δ |
| 126 | TSAR-N3 | PCR | R | 1Δ | 0 | 0 | 0 | 1Δ |

TABLE 2-continued

ID with sources, ampicillin resistance (AMP-R), the selected 4 NGS-identified AMP-R genes,
and the universal stdA gene in the 169 NTS isolates from TMU-SHH and TSAR at NHRI for the
PCR study (Δ = correct prediction; R = Resistant to ampicillin; S = Susceptible to ampicillin;
1 = detected; 0 = not detected).

| No. | ID | Method | AMP-R | bla$_{TEM-1b}$ | bla$_{CARB-2}$ | bla$_{CMY-2}$ | ampC | stdA |
|---|---|---|---|---|---|---|---|---|
| 127 | TSAR-N4 | PCR | R | 0 | 1Δ | 0 | 0 | 1Δ |
| 128 | TSAR-N6 | PCR | R | 0 | 1Δ | 0 | 0 | 1Δ |
| 129 | TSAR-N7 | PCR | R | 0 | 1Δ | 0 | 0 | 1Δ |
| 130 | TSAR-N10 | PCR | R | 1Δ | 0 | 0 | 0 | 1Δ |
| 131 | TSAR-N11 | PCR | R | 1Δ | 0 | 0 | 0 | 1Δ |
| 132 | TSAR-N12 | PCR | R | 0 | 1Δ | 0 | 0 | 1Δ |
| 133 | TSAR-N13 | PCR | R | 0 | 1Δ | 0 | 0 | 1Δ |
| 134 | TSAR-N14 | PCR | R | 0 | 1Δ | 0 | 0 | 1Δ |
| 135 | TSAR-N17 | PCR | R | 0 | 1Δ | 0 | 0 | 1Δ |
| 136 | TSAR-N18 | PCR | R | 0 | 1Δ | 0 | 0 | 1Δ |
| 137 | TSAR-N20 | PCR | R | 1Δ | 1Δ | 1Δ | 1Δ | 1Δ |
| 138 | TSAR-N21 | PCR | S | 0Δ | 0Δ | 0Δ | 0Δ | 1Δ |
| 139 | TSAR-N22 | PCR | S | 0Δ | 0Δ | 0Δ | 0Δ | 1Δ |
| 140 | TSAR-N23 | PCR | S | 0Δ | 0Δ | 0Δ | 0Δ | 1Δ |
| 141 | TSAR-N24 | PCR | S | 0Δ | 0Δ | 0Δ | 0Δ | 1Δ |
| 142 | TSAR-N25 | PCR | S | 0Δ | 0Δ | 0Δ | 0Δ | 1Δ |
| 143 | TSAR-N26 | PCR | S | 0Δ | 0Δ | 0Δ | 0Δ | 1Δ |
| 144 | TSAR-N27 | PCR | S | 0Δ | 0Δ | 0Δ | 0Δ | 1Δ |
| 145 | TSAR-N28 | PCR | S | 0Δ | 0Δ | 0Δ | 0Δ | 1Δ |
| 146 | TSAR-N29 | PCR | S | 0Δ | 0Δ | 0Δ | 0Δ | 1Δ |
| 147 | TSAR-N30 | PCR | S | 0Δ | 0Δ | 0Δ | 0Δ | 1Δ |
| 148 | TSAR-S1 | PCR | R | 1Δ | 0 | 0 | 0 | 1Δ |
| 149 | TSAR-S2 | PCR | R | 1Δ | 0 | 0 | 0 | 1Δ |
| 150 | TSAR-S3 | PCR | R | 1Δ | 0 | 0 | 0 | 1Δ |
| 151 | TSAR-S4 | PCR | R | 1Δ | 0 | 0 | 0 | 1Δ |
| 152 | TSAR-S5 | PCR | R | 1Δ | 0 | 0 | 0 | 1Δ |
| 153 | TSAR-S6 | PCR | R | 1Δ | 0 | 0 | 0 | 1Δ |
| 154 | TSAR-S7 | PCR | R | 0 | 1Δ | 0 | 0 | 1Δ |
| 155 | TSAR-S8 | PCR | R | 1Δ | 0 | 0 | 0 | 1Δ |
| 156 | TSAR-S9 | PCR | R | 0 | 1Δ | 0 | 0 | 1Δ |
| 157 | TSAR-S10 | PCR | R | 1Δ | 0 | 0 | 0 | 1Δ |
| 158 | TSAR-S11 | PCR | R | 1Δ | 0 | 0 | 0 | 1Δ |
| 159 | TSAR-S12 | PCR | R | 1Δ | 0 | 0 | 0 | 1Δ |
| 160 | TSAR-S21 | PCR | S | 0Δ | 0Δ | 0Δ | 0Δ | 1Δ |
| 161 | TSAR-S22 | PCR | S | 0Δ | 0Δ | 0Δ | 0Δ | 1Δ |
| 162 | TSAR-S23 | PCR | S | 0Δ | 0Δ | 0Δ | 0Δ | 1Δ |
| 163 | TSAR-S24 | PCR | S | 0Δ | 0Δ | 0Δ | 0Δ | 1Δ |
| 164 | TSAR-S25 | PCR | S | 0Δ | 0Δ | 0Δ | 0Δ | 1Δ |
| 165 | TSAR-S26 | PCR | S | 0Δ | 0Δ | 0Δ | 0Δ | 1Δ |
| 166 | TSAR-S27 | PCR | S | 0Δ | 0Δ | 0Δ | 0Δ | 1Δ |
| 167 | TSAR-S28 | PCR | S | 0Δ | 0Δ | 0Δ | 0Δ | 1Δ |
| 168 | TSAR-S29 | PCR | S | 0Δ | 0Δ | 0Δ | 0Δ | 1Δ |
| 169 | TSAR-S30 | PCR | S | 0Δ | 0Δ | 0Δ | 0Δ | 1Δ |

Before the NGS study, the antimicrobial susceptibility to ampicillin in the 169 isolates was re-confirmed using the disc inhibition zones or MICs (FIG. 1). Then, the bacterial DNAs were extracted from 53 NTS isolates and NGS was performed using the Illumina© MiSeq sequencer. Subsequently, the NTS serotypes of 53 NTS clinical isolates were confirmed by multilocus sequence typing (MLST) as shown in Table 1. The big genomic data were analyzed to examine presence of plasmid-mediated genes or genetic mutations in the bacterial genome of *Salmonella* spp. and other bacteria reported in the PubMed, ARG-ANNOT, CARD, and Res-Finder (FIG. 1).

3. Antibiotics Susceptibility Test

The 169 NTS clinical isolates were tested for antimicrobial susceptibility based on (CLSI) guidelines. Briefly, bacteria were spread onto Mueller-Hinton MH agar, and co-incubated with antimicrobial disks (Oxoid, Cambridge, UK) of ampicillin individually at 37° C. for 18 hours. Another alternative is measurement of the minimum inhibitory concentrations (MICs) of ampicillin in serial dilutions of ampicillin co-cultured with bacterial solution of NTS isolates. Finally, the resistance to ampicillin in NTS isolates was determined according to the diameter of inhibition zone (≤13 mm) and/or the MIC of ampicillin>16 μg/mL according to the guideline of CLSI.

4. Genomic DNA Isolation

The genomic DNA from the 169 NTS clinical isolates were purified using Genomic DNA isolation kit (GeneMark, Taichung, Taiwan) according to the manuscript. Briefly, total 5 ml of each *Salmonella* isolate was culture in LB broth and incubated at 37° C. overnight. Then the bacteria were collected by centrifugation at 13,000 rpm, and the supernatants were discarded. Next, the bacterial pellet was lysed using lysis buffer containing lysozyme provided by kit, and flow through the spin column. Finally, the genomic DNA of each *Salmonella* isolate was eluted in ddH$_2$O. The quality of genomic DNA was examined using DS-11 FX Spectrophotometer (DeNovix, Wilmington, DE).

5. Next-Generation Sequencing (NGS)

The next-generation sequencing was performed using MiSeq (Illumina, San Diego, CA) according to the manuscript. Briefly, each 0.5 μg genomic DNA purified from bacterial clinical isolates was sheared using Covaris S2 ultrasonicator (Covaris, Woburn, MA) for fragmenting DNA into small pieces at first. Subsequently, the sheared DNA was end-repaired by T4 polynucleotide kinase, T4 DNA polymerase, and Klenow enzyme (Illumina) according to manuscript to construct the DNA library. Then, the DNA pool was purified with magnetic beads (Life Technologies, Carlsbad, CA) to remove the unrepaired DNA. Finally, the purified DNA was used for NGS.

6. Sequencing Data Processing

After filtering of low quality reads with R ShortRead package (quality>20 and length>270 base pairs), the sequences were de novo assembled using Velvet then reordered and concatenated with Artemis Comparison Tool (ACT) against *Salmonella enterica* subsp. *enterica* serovar *Typhimurium* SL1344 complete genome (NCBI Reference Sequence: NC_016810.1), a known isolate to have multiple antimicrobial resistance.

7. PCR Validation of the NGS-Identified 4 Genes and stdA in the 169 NTS Clinical Isolates We conducted PCR of the 4 NGS-identified genes and stdA using the following pairs of primer sequences:

```
(i) bla_TEM-1b-F
                             (SEQ ID NO 1)
(5'-ACGCTCGTCGTTTGGTATG-3') and bla_TEM-1b-R
                             (SEQ ID NO 2)
(5'- TGCTATGTGGTGCGGTATT-3');

(ii) blacARB-2-F
                             (SEQ ID NO 3)
(5'-TAGAAAAGCAAGTAGGGCAGG-3') and blacARB-2-R
                             (SEQ ID NO 4)
(5'-AGATAGCGCGGAACCAAATAA-3');

(iii) blacMY-2-F
                             (SEQ ID NO 5)
(5'-CGCAGAACGAACAAAAAGAT-3') and blacMY-2-R
                             (SEQ ID NO 6)
(5'-AATACGCCAGTAGCGAGACT-3');

(iv) ampC-F
                             (SEQ ID NO 7)
(5'-TGAGCCACACCTGGATTA-3') and ampC-R
                             (SEQ ID NO 8)
(5'-CCCTGCCGCAGATTTTTA-3');

(v) stdA-F
                             (SEQ ID NO 9)
(5'-TCACAGGTATTTCAGAGTGTAGG-3') and stdA-R
                             (SEQ ID NO 10)
(5'-CAGTCGATCCACCAACAGCAGG-3').
```

The PCR was performed using ABI PCR Thermal Cycler 2720 (Applied Biosystems, Foster, CA), and the PCR condition was set as 1 cycle of 95° C. for 3 minutes (denaturing step), 35 cycles of 95° C. for 45 seconds, 56° C. for 45 seconds, and 72° C. for 45 seconds (annealing step), 1 cycle of 72° C. for 7 minutes (extension step), and finally hold at 10° C. The amplified fragments were observed by 1.3% agarose gel in 1×TBE (Tris-borate-EDTA) buffer.

8. Data Analysis

Acquired resistance genes were identified via PubMed, ARG-ANNOT, CARD, and ResFinder (criteria: sequence identity≥90% in at least 60% of the length of the gene sequences). Genes reported in association with ampicillin resistance were selected and the reference sequences were downloaded from gene databases [Accession numbers: bla_TEM-1b, AY458016 (SEQ ID NO 11); bla_OXA-1, HQ170510 (SEQ ID NO 12); bla_CARB-2, M69058 (SEQ ID NO 13); bla_TEM-227, KY418040 (SEQ ID NO 14); bla_CMY-2, X91840 (SEQ ID NO 15); ampC, NC_000913.3:c4378944-4377811 (SEQ ID NO 16); bla_CTX-M-9, AF174129 (SEQ ID NO 17); bla_SHV-1, AF148850 (SEQ ID NO 18); bla_FOX-6, AY034848 (SEQ ID NO 19); bla_PER-2, X93314 (SEQ ID NO 20); and bla_CTX-M-15, AY044436 (SEQ ID NO 21)]. The accession number of the fimbrial adhesion gene stdA is NC_003197.2:c3191849-3191126 (SEQ ID NO 22). We aligned the reference gene sequences with the sequences of the genes from our isolates using NCBI BLAST+ 2.2.31 command line tool. Then we used CLC sequence viewer (CLC Bio; Qiagen) to visualize the data.

Results

Our NGS study demonstrated that the fimbrial adhesion gene stdA for identification of NTS is present in all the 53 NTS isolates (Tables 1 & 3). Furthermore, our PCR study also confirmed that stdA is present in all the 169 NTS isolates (Table 2).

TABLE 3

Universal identification of the stdA gene in the 53 NTS isolates using NGS.

| No. | Query ID | NTS isolate ID | % Identity | Alignment length (bp) | Mismatches (bp) |
|---|---|---|---|---|---|
| 1 | NC_003197.2:c3191849-3191126 | SH-A1 | 89.0 | 728 | 69 |
| 2 | NC_003197.2:c3191849-3191126 | SH-B2 | 88.2 | 684 | 69 |
| 3 | NC_003197.2:c3191849-3191126 | SH-B5 | 89.0 | 728 | 69 |
| 4 | NC_003197.2:c3191849-3191126 | SH-C2 | 88.9 | 728 | 70 |
| 5 | NC_003197.2:c3191849-3191126 | SH-C3 | 89.0 | 728 | 69 |
| 6 | NC_003197.2:c3191849-3191126 | SH-C4 | 99.9 | 724 | 1 |
| 7 | NC_003197.2:c3191849-3191126 | SH-D2 | 89.0 | 728 | 69 |
| 8 | NC_003197.2:c3191849-3191126 | SH-D4 | 89.0 | 728 | 69 |
| 9 | NC_003197.2:c3191849-3191126 | SH-D5 | 99.9 | 724 | 1 |
| 10 | NC_003197.2:c3191849-3191126 | SH-E1 | 87.2 | 592 | 65 |
| 11 | NC_003197.2:c3191849-3191126 | SH-E2 | 99.7 | 724 | 2 |
| 12 | NC_003197.2:c3191849-3191126 | SH-E3 | 88.9 | 728 | 70 |
| 13 | NC_003197.2:c3191849-3191126 | SH-F4 | 100.0 | 724 | 0 |
| 14 | NC_003197.2:c3191849-3191126 | SH-F5 | 89.0 | 728 | 69 |
| 15 | NC_003197.2:c3191849-3191126 | SH-G1 | 87.4 | 729 | 82 |
| 16 | NC_003197.2:c3191849-3191126 | SH-G2 | 100.0 | 724 | 0 |
| 17 | NC_003197.2:c3191849-3191126 | SH-G3 | 89.0 | 728 | 69 |
| 18 | NC_003197.2:c3191849-3191126 | SH-G5 | 99.0 | 724 | 7 |
| 19 | NC_003197.2:c3191849-3191126 | SH-H3 | 96.1 | 724 | 28 |
| 20 | NC_003197.2:c3191849-3191126 | SH-H4 | 86.4 | 595 | 70 |
| 21 | NC_003197.2:c3191849-3191126 | SH-I2 | 89.2 | 732 | 66 |
| 22 | NC_003197.2:c3191849-3191126 | TSAR-C1 | 94.7 | 731 | 28 |
| 23 | NC_003197.2:c3191849-3191126 | TSAR-C10 | 94.8 | 731 | 27 |
| 24 | NC_003197.2:c3191849-3191126 | TSAR-C13 | 87.4 | 729 | 82 |
| 25 | NC_003197.2:c3191849-3191126 | TSAR-C16 | 100.0 | 724 | 0 |
| 26 | NC_003197.2:c3191849-3191126 | TSAR-C19 | 87.4 | 729 | 82 |
| 27 | NC_003197.2:c3191849-3191126 | TSAR-C2 | 94.7 | 731 | 28 |
| 28 | NC_003197.2:c3191849-3191126 | TSAR-C3 | 94.7 | 731 | 28 |
| 29 | NC_003197.2:c3191849-3191126 | TSAR-C4 | 100.0 | 724 | 0 |
| 30 | NC_003197.2:c3191849-3191126 | TSAR-C5 | 99.9 | 724 | 1 |
| 31 | NC_003197.2:c3191849-3191126 | TSAR-C6 | 99.9 | 724 | 1 |
| 32 | NC_003197.2:c3191849-3191126 | TSAR-C7 | 100.0 | 724 | 0 |
| 33 | NC_003197.2:c3191849-3191126 | TSAR-E10 | 100.0 | 724 | 0 |
| 34 | NC_003197.2:c3191849-3191126 | TSAR-E16 | 89.8 | 728 | 63 |
| 35 | NC_003197.2:c3191849-3191126 | TSAR-E18 | 96.3 | 724 | 27 |
| 36 | NC_003197.2:c3191849-3191126 | TSAR-E19 | 88.9 | 728 | 70 |
| 37 | NC_003197.2:c3191849-3191126 | TSAR-E20 | 99.9 | 724 | 1 |
| 38 | NC_003197.2:c3191849-3191126 | TSAR-E5 | 99.9 | 724 | 1 |
| 39 | NC_003197.2:c3191849-3191126 | TSAR-E9 | 99.9 | 708 | 1 |
| 40 | NC_003197.2:c3191849-3191126 | TSAR-N15 | 94.7 | 731 | 28 |
| 41 | NC_003197.2:c3191849-3191126 | TSAR-N16 | 100.0 | 724 | 0 |
| 42 | NC_003197.2:c3191849-3191126 | TSAR-N19 | 89.0 | 728 | 69 |

19

TABLE 3-continued

Universal identification of the stdA gene in the 53 NTS isolates using NGS.

| No. | Query ID | NTS isolate ID | % Identity | Alignment length (bp) | Mismatches (bp) |
|---|---|---|---|---|---|
| 43 | NC_003197.2:c3191849-3191126 | TSAR-N5 | 100.0 | 724 | 0 |
| 44 | NC_003197.2:c3191849-3191126 | TSAR-N8 | 100.0 | 724 | 0 |
| 45 | NC_003197.2:c3191849-3191126 | TSAR-N9 | 94.7 | 731 | 28 |
| 46 | NC_003197.2:c3191849-3191126 | TSAR-S13 | 99.0 | 724 | 7 |
| 47 | NC_003197.2:c3191849-3191126 | TSAR-S14 | 100.0 | 724 | 0 |
| 48 | NC_003197.2:c3191849-3191126 | TSAR-S15 | 89.0 | 728 | 69 |
| 49 | NC_003197.2:c3191849-3191126 | TSAR-S16 | 88.0 | 734 | 74 |
| 50 | NC_003197.2:c3191849-3191126 | TSAR-S17 | 88.9 | 728 | 70 |
| 51 | NC_003197.2:c3191849-3191126 | TSAR-S18 | 88.9 | 728 | 70 |
| 52 | NC_003197.2:c3191849-3191126 | TSAR-S19 | 88.0 | 734 | 74 |
| 53 | NC_003197.2:c3191849-3191126 | TSAR-S20 | 93.8 | 728 | 40 |

Our NGS pilot study discovered that at least one or more genes among the 7-gene combination ($\text{bla}_{TEM-1b}$, $\text{bla}_{OXA-1}$, $\text{bla}_{CARB-2}$, $\text{bla}_{TEM-227}$, $\text{bla}_{CMY-2}$, ampC, and $\text{bla}_{CTX-M-9}$) are universally present in the 42 AMP-R NTS isolates after comparison of their whole genome sequences with those of the 11 AMP-S NTS isolates (Table 1). The $\text{bla}_{TEM-1b}$ gene encodes the protein belonging to Bush-Jacoby group 2b subclass A (e.g. TEM, SHV-1), the $\text{bla}_{OXA-1}$ encode the protein classified as Bush-Jacoby group 2d, the $\text{bla}_{CARB-2}$ gene encode the protein in the Bush-Jacoby group 2c

20 high diversity of CR1-bearing class 1 integrons linked to different Tn402 derivatives, often to Tn21, and the presence of $\text{bla}_{CTX-M-9}$ on broad-host-range IncP-1α plasmids might contribute to its dissemination to hosts that were not members of the family Enterobacteriaceae [29]. The locally-acquired human isolates of *S. Typhimurium* carrying $\text{bla}_{CTX-M-9}$ were identified to be of bovine origin, raising concerns about the human impact of the off-label use of antibiotics in cattle [30]. So far, the $\text{bla}_{TEM-227}$ gene has not been reported to be associated with AMP-R in NTS.

For individual single gene of the 7-gene combination ($\text{bla}_{TEM-1b}$, $\text{bla}_{OXA-1}$, $\text{bla}_{CARB-2}$, $\text{bla}_{TEM-227}$, $\text{bla}_{CMY-2}$, ampC, and $\text{bla}_{CTX-M-9}$) to predict AMP-R in 53 NGS isolates, the specificity is 100% but the sensitivity ranged from 2% to 52%, and the accuracy of prediction rates ranged from 21% to 62% (white, Table 4). However, we selected other 4 ampicillin resistance genes ($\text{bla}_{SHV-1}$ [31], $\text{bla}_{FOX-6}$ [32], $\text{bla}_{PER-2}$ [33], and $\text{bla}_{CTX-M-15}$ [34]) that were also detected in AMP-R NTS isolates for comparison. For any single-gene of these four comparative genes ($\text{bla}_{SHV-1}$, $\text{bla}_{FOX-6}$, $\text{bla}_{PER-2}$, and $\text{bla}_{CTX-M-15}$) to predict AMP-R in 53 NGS isolates, the specificity is 100% but the sensitivity of the latter 4 genes for detection of ampicillin resistance was 0% and their correct prediction rates were only 21% (white, Table 4).

TABLE 4

NGS data from the 53 NTS isolates for one-gene or two-gene prediction for ampicillin resistance. Comparison in sensitivity, specificity, positive prediction value (PPV), negative prediction value (NPV), and accuracy of prediction rates between using the 7 targeted genes and the other 4 ampicillin resistance genes for their detection of ampicillin resistance in the 53 NTS isolates. Other 2-gene combinations with accuracy <60% are not listed.

| $\text{bla}_{TEM-1B}$ | $\text{bla}_{OXA-1}$ | $\text{bla}_{CARB-2}$ | $\text{bla}_{TEM-227}$ | $\text{bla}_{CMY-2}$ | ampC | $\text{bla}_{CTX-M-9}$ | $\text{bla}_{SHV-1}$ | $\text{bla}_{FOX-6}$ | $\text{bla}_{PER-2}$ | $\text{bla}_{CTX-M-15}$ | Specificity | Sensitivity | NPV | PPV | Accuracy |
|---|---|---|---|---|---|---|---|---|---|---|---|---|---|---|---|
| + | | | | | | | | | | | 100% | 52% | 35% | 100% | 62% |
| | + | | | | | | | | | | 100% | 14% | 23% | 100% | 32% |
| | | + | | | | | | | | | 100% | 10% | 22% | 100% | 28% |
| | | | + | | | | | | | | 100% | 2% | 21% | 100% | 23% |
| | | | | + | | | | | | | 100% | 5% | 22% | 100% | 25% |
| | | | | | + | | | | | | 100% | 5% | 22% | 100% | 25% |
| | | | | | | + | | | | | 100% | 2% | 21% | 100% | 23% |
| | | | | | | | + | | | | 100% | 0% | 21% | NA | 21% |
| | | | | | | | | + | | | 100% | 0% | 21% | NA | 21% |
| | | | | | | | | | + | | 100% | 0% | 21% | NA | 21% |
| | | | | | | | | | | + | 100% | 0% | 21% | NA | 21% |
| + | + | | | | | | | | | | 100% | 64% | 42% | 100% | 72% |
| + | | + | | | | | | | | | 100% | 62% | 41% | 100% | 70% |
| + | | | + | | | | | | | | 100% | 55% | 37% | 100% | 64% |
| + | | | | + | | | | | | | 100% | 55% | 37% | 100% | 64% |
| + | | | | | + | | | | | | 100% | 55% | 37% | 100% | 64% |
| + | | | | | | + | | | | | 100% | 52% | 35% | 100% | 62% |
| + | | | | | | | + | | | | 100% | 52% | 35% | 100% | 62% |
| + | | | | | | | | + | | | 100% | 52% | 35% | 100% | 62% |
| + | | | | | | | | | + | | 100% | 52% | 35% | 100% | 62% |
| + | | | | | | | | | | + | 100% | 52% | 35% | 100% | 62% |
| | | | + | + | | | | | | | 100% | 7% | 22% | 100% | 26% |
| | | | | + | + | | | | | | 100% | 5% | 22% | 100% | 25% |
| | | | | | + | + | | | | | 100% | 7% | 22% | 100% | 26% |
| | | | | | | | + | + | | | 100% | 0% | 21% | NA | 21% |
| | | | | | | | + | | + | | 100% | 0% | 21% | NA | 21% |
| | | | | | | | + | | | + | 100% | 0% | 21% | NA | 21% |
| | | | | | | | | + | + | | 100% | 0% | 21% | NA | 21% |
| | | | | | | | | + | | + | 100% | 0% | 21% | NA | 21% |
| | | | | | | | | | + | + | 100% | 0% | 21% | NA | 21% | subclass A (e.g. PSE-1, CARB-3), and the $\text{bla}_{CMY-2}$ and ampC encode the proteins classified as Bush-Jacoby group 1 subclass C (e.g. AmpC, CMY-2) [28]. The $\text{bla}_{CTX-M-9}$ in a If we use the 2-gene panel ($\text{bla}_{TEM-1b}$ and $\text{bla}_{OXA-1}$, or $\text{bla}_{TEM-1b}$ and $\text{bla}_{CARB-2}$) from the 7-gene combination ($\text{bla}_{TEM-1b}$, $\text{bla}_{OXA-1}$, $\text{bla}_{CARB-2}$, $\text{bla}_{TEM-227}$, $\text{bla}_{CMY-2}$, ampC,

21 and $bla_{CTX-M-9}$) to predict AMP-R in 53 NGS isolates, the specificity is 100% but the sensitivity increased to 64% and 62%, respectively, and the accuracy of prediction rates increased to 72% and 70%, respectively (light gray, Table 4). If we use $bla_{TEM-1b}$ and any one of the other four genes ($bla_{TEM-227}$, $bla_{CMY-2}$, ampC, and $bla_{CTX-M-9}$) or the four comparative genes ($bla_{SHV-1}$, $bla_{FOX-6}$, $bla_{PER-2}$, and $bla_{CTX-M-15}$) in the 2-gene panel to predict AMP-R in 53 NGS isolates, the accuracy of prediction rates ranged between 62% to 64% (light gray, Table 4). If any two genes of the other four genes the other four genes ($bla_{TEM-227}$, $bla_{CMY-2}$, ampC, and $bla_{CTX-M-9}$) or the four comparative genes ($bla_{SHV-1}$, $bla_{FOX-6}$, $bla_{PER-2}$, and $bla_{CTX-M-15}$) are used in the 2-gene panel to predict AMP-R in 53 NGS isolates, the accuracy of prediction rates is as low as 25-26% and 21%, respectively (dark gray and gray, Table 4).

If we use the 3-gene panel ($bla_{TEM-1b}$, $bla_{OXA-1}$, and $bla_{CARB-2}$) from the 7-gene combination to predict AMP-R in 53 NGS isolates, the specificity is 100% and the sensitivity is 74%, respectively, and the accuracy of prediction rates increased to 79% (first line, Table 5).

If we use the 3-gene panel ($bla_{TEM-1b}$, $bla_{OXA-1}$, and one of $bla_{TEM-227}$, $bla_{CMY-2}$, ampC, and $bla_{CTX-M-9}$; or $bla_{TEM-1b}$ and $bla_{CARB-2}$, and one of $bla_{TEM-227}$, $bla_{CMY-2}$, ampC, and $bla_{CTX-M-9}$) from the 7-gene combination to predict AMP-R in 53 NGS isolates, the specificity is 100% and the sensitivity ranged between 62% and 67%, respectively, and the accuracy of prediction rates ranged between 72% and 74% (2nd to 17th lines, Table 5).

If we use any three of the other four genes ($bla_{TEM-227}$, $bla_{CMY-2}$, ampC, and $bla_{CTX-M-9}$) without $bla_{TEM-1b}$, $bla_{OXA-1}$, and $bla_{CARB-2}$ in the 3-gene panel to predict AMP-R in 53 NGS isolates, the sensitivity is as low as 7-10% and the accuracy of prediction rates dropped to 26% to 28% (18th to 19th lines, Table 5). If we use any three of the four comparative genes ($bla_{SHV-1}$, $bla_{FOX-6}$, $bla_{PER-2}$, and $bla_{CTX-M-15}$) without $bla_{TEM-1b}$, $bla_{OXA-1}$, and $bla_{CARB-2}$ in the 3-gene panel to predict AMP-R in 53 NGS isolates, the sensitivity is 0% and the accuracy of prediction is only 21% (20th to 23rd lines, Table 5).

TABLE 5

NGS data from the 53 NTS isolates for three-gene prediction for ampicillin resistance.

| $bla_{TEM-1B}$ | $bla_{OXA-1}$ | $bla_{CARB-2}$ | $bla_{TEM-227}$ | $bla_{CMY-2}$ | ampC | $bla_{CTX-M-9}$ | $bla_{SHV-1}$ | $bla_{FOX-6}$ | $bla_{PER-2}$ | $bla_{CTX-M-15}$ | Specificity | Sensitivity | NPV | PPV | Accuracy |
|---|---|---|---|---|---|---|---|---|---|---|---|---|---|---|---|
| + | + | + |   |   |   |   |   |   |   |   | 100% | 74% | 50% | 100% | 79% |
| + | + |   | + |   |   |   |   |   |   |   | 100% | 67% | 44% | 100% | 74% |
| + | + |   |   | + |   |   |   |   |   |   | 100% | 67% | 44% | 100% | 74% |
| + | + |   |   |   | + |   |   |   |   |   | 100% | 67% | 44% | 100% | 74% |
| + | + |   |   |   |   | + |   |   |   |   | 100% | 64% | 42% | 100% | 72% |
| + | + |   |   |   |   |   | + |   |   |   | 100% | 64% | 42% | 100% | 72% |
| + | + |   |   |   |   |   |   | + |   |   | 100% | 64% | 42% | 100% | 72% |
| + | + |   |   |   |   |   |   |   | + |   | 100% | 64% | 42% | 100% | 72% |
| + | + |   |   |   |   |   |   |   |   | + | 100% | 64% | 42% | 100% | 72% |
| + |   | + | + |   |   |   |   |   |   |   | 100% | 64% | 42% | 100% | 72% |
| + |   | + |   | + |   |   |   |   |   |   | 100% | 64% | 42% | 100% | 72% |
| + |   | + |   |   | + |   |   |   |   |   | 100% | 64% | 42% | 100% | 72% |
| + |   | + |   |   |   | + |   |   |   |   | 100% | 62% | 41% | 100% | 70% |
| + |   | + |   |   |   |   | + |   |   |   | 100% | 62% | 41% | 100% | 70% |
| + |   | + |   |   |   |   |   | + |   |   | 100% | 62% | 41% | 100% | 70% |
| + |   | + |   |   |   |   |   |   | + |   | 100% | 62% | 41% | 100% | 70% |
| + |   | + |   |   |   |   |   |   |   | + | 100% | 62% | 41% | 100% | 70% |
|   |   |   | + | + | + |   |   |   |   |   | 100% | 7% | 22% | 100% | 26% |
|   |   |   | + | + |   | + |   |   |   |   | 100% | 10% | 22% | 100% | 28% |
|   |   |   |   |   |   |   | + | + | + |   | 100% | 0% | 21% | NA | 21% |
|   |   |   |   |   |   |   | + | + |   | + | 100% | 0% | 21% | NA | 21% |
|   |   |   |   |   |   |   | + |   | + | + | 100% | 0% | 21% | NA | 21% |
|   |   |   |   |   |   |   |   | + | + | + | 100% | 0% | 21% | NA | 21% |

Other 3-gene combinations with accuracy<70% are not listed.

If we use the 4-gene panel ($bla_{TEM-1b}$, $bla_{OXA-1}$, $bla_{CARB-2}$, and the one gene is selected from the group consisting of $bla_{TEM-227}$, $bla_{CMY2}$, and ampC from the 7-gene combination to predict AMP-R in the 53 NTS isolates, the specificity is 100% and the sensitivity is 76%, respectively, and the accuracy of prediction rates increased to 81% (light gray, Table 6).

TABLE 6

NGS data from the 53 NTS isolates for four-gene prediction for ampicillin resistance. Other 4-gene combinations with accuracy <75% are not listed.

| $bla_{TEM-1B}$ | $bla_{OXA-1}$ | $bla_{CARB-2}$ | $bla_{TEM-227}$ | $bla_{CMY-2}$ | ampC | $bla_{CTX-M-9}$ | $bla_{SHV-1}$ | $bla_{FOX-6}$ | $bla_{PER-2}$ | $bla_{CTX-M-15}$ | Specificity | Sensitivity | NPV | PPV | Accuracy |
|---|---|---|---|---|---|---|---|---|---|---|---|---|---|---|---|
| + | + | + | + |   |   |   |   |   |   |   | 100% | 76% | 52% | 100% | 81% |
| + | + | + |   | + |   |   |   |   |   |   | 100% | 76% | 53% | 100% | 81% |
| + | + | + |   |   | + |   |   |   |   |   | 100% | 76% | 52% | 100% | 81% |

TABLE 6-continued

NGS data from the 53 NTS isolates for four-gene prediction for ampicillin resistance. Other
4-gene combinations with accuracy <75% are not listed.

| $bla_{TEM-1B}$ | $bla_{OXA-1}$ | $bla_{CARB-2}$ | $bla_{TEM-227}$ | $bla_{CMY-2}$ | ampC | $bla_{CTX-M-9}$ | $bla_{SHV-1}$ | $bla_{FOX-6}$ | $bla_{PER-2}$ | $bla_{CTX-M-15}$ | Specificity | Sensitivity | NPV | PPV | Accuracy |
|---|---|---|---|---|---|---|---|---|---|---|---|---|---|---|---|
| + | + | + |  |  |  | + |  |  |  |  | 100% | 74% | 50% | 100% | 79% |
| + | + | + |  |  |  |  | + |  |  |  | 100% | 74% | 58% | 100% | 79% |
| + | + | + |  |  |  |  |  | + |  |  | 100% | 74% | 50% | 100% | 79% |
| + | + | + |  |  |  |  |  |  | + |  | 100% | 74% | 50% | 100% | 79% |
| + | + | + |  |  |  |  |  |  |  | + | 100% | 74% | 50% | 100% | 79% |
| + | + |  | + | + |  |  |  |  |  |  | 100% | 69% | 46% | 100% | 79% |
| + | + |  | + |  | + |  |  |  |  |  | 100% | 69% | 46% | 100% | 75% |
| + | + |  |  |  |  |  | + | + |  |  | 100% | 64% | 42% | 100% | 75% |
| + | + |  |  |  |  |  | + |  | + |  | 100% | 64% | 42% | 100% | 72% |
|  |  |  | + | + | + | + |  |  |  |  | 100% | 10% | 22% | 100% | 28% |
|  |  |  | + | + | + |  | + |  |  |  | 100% | 7% | 22% | 100% | 26% |
|  |  |  |  |  |  | + | + | + | + |  | 100% | 2% | 21% | 100% | 23% |
|  |  |  |  |  |  | + | + | + |  | + | 100% | 2% | 21% | 100% | 23% |
|  |  |  |  |  |  | + | + |  | + | + | 100% | 2% | 21% | 100% | 23% |
|  |  |  |  |  |  | + |  | + | + | + | 100% | 2% | 21% | 100% | 23% |
|  |  |  |  |  |  |  | + | + | + | + | 100% | 0% | 21% | NA | 21% |

If we use any four of the other four genes ($bla_{TEM-227}$, $bla_{CMY-2}$, ampC, and $bla_{CTX-M-9}$) and the four comparative genes ($bla_{SHV-1}$, $bla_{FOX-6}$, $bla_{PER-2}$, and $bla_{CTX-M-15}$) without $bla_{TEM-1b}$, $bla_{OXA-1}$, and $bla_{CARB-2}$ in the 4-gene panel to predict AMP-R in the 53 NTS isolates, the sensitivity is 0-10% and the accuracy of prediction is only 21-28% (13th to 14th lines and 15th to 19th lines, Table 6).

If we use the 5-gene panel ($bla_{TEM-1b}$, $bla_{OXA-1}$, $bla_{CARB-2}$, $bla_{TEM-227}$, and the one gene is selected from the group consisting of $bla_{CMY-2}$ and ampC) from the 7-gene combination to predict AMP-R in the 53 NTS isolates, the specificity is 100% and the sensitivity is 79%, respectively, and the accuracy of prediction rates increased to 83% (1st to 2nd lines, top, Table 7).

If we use the 6-gene panel ($bla_{TEM-1b}$, $bla_{OXA-1}$, $bla_{CARB-2}$, $bla_{TEM-227}$, $bla_{CMY-2}$, and the one gene is selected from the group consisting of ampC and $bla_{CTX-M-9}$) from the 7-gene combination to predict AMP-R in the 53 NTS isolates, the specificity is 100% and the sensitivity is 79%, and the accuracy of prediction rates increased to 83% (9th to 10th lines, middle, Table 7).

If we use the 7-gene panel ($bla_{TEM-1b}$, $bla_{OXA-1}$, $bla_{CARB-2}$, $bla_{TEM-227}$, $bla_{CMY-2}$, ampC, and $bla_{CTX-M-9}$) from the 7-gene combination to predict AMP-R in the 53 NTS isolates, the specificity is 100% and the sensitivity is 79%, and the accuracy of prediction rates increased to 83% (16th lines, low, Table 7).

TABLE 7

NGS data from the 53 NTS isolates for five-gene prediction for ampicillin resistance.

| $bla_{TEM-1B}$ | $bla_{OXA-1}$ | $bla_{CARB-2}$ | $bla_{TEM-227}$ | $bla_{CMY-2}$ | ampC | $bla_{CTX-M-9}$ | $bla_{SHV-1}$ | $bla_{FOX-6}$ | $bla_{PER-2}$ | $bla_{CTX-M-15}$ | Specificity | Sensitivity | NPV | PPV | Accuracy |
|---|---|---|---|---|---|---|---|---|---|---|---|---|---|---|---|
| + | + | + | + | + |  |  |  |  |  |  | 100% | 79% | 55% | 100% | 83% |
| + | + | + | + |  | + |  |  |  |  |  | 100% | 79% | 55% | 100% | 83% |
| + | + |  | + | + | + |  |  |  |  |  | 100% | 69% | 46% | 100% | 75% |
| + | + |  | + | + |  | + |  |  |  |  | 100% | 69% | 46% | 100% | 75% |
| + |  | + | + | + | + |  |  |  |  |  | 100% | 67% | 44% | 100% | 74% |
| + |  | + | + | + |  | + |  |  |  |  | 100% | 67% | 44% | 100% | 74% |
|  |  |  |  |  | + |  | + | + | + | + | 100% | 5% | 22% | 100% | 25% |
|  |  |  |  |  |  | + | + | + | + | + | 100% | 2% | 21% | 100% | 23% |
| + | + | + | + | + | + |  |  |  |  |  | 100% | 79% | 55% | 100% | 83% |
| + | + | + | + | + |  | + |  |  |  |  | 100% | 79% | 55% | 100% | 83% |
| + | + |  | + | + | + | + |  |  |  |  | 100% | 69% | 46% | 100% | 75% |
| + |  | + | + | + | + | + |  |  |  |  | 100% | 67% | 44% | 100% | 74% |
|  |  |  |  |  | + | + | + | + | + | + | 100% | 5% | 22% | 100% | 25% |
|  |  |  |  | + |  | + | + | + | + | + | 100% | 7% | 22% | 100% | 26% |
|  |  |  |  | + | + | + | + | + | + | + | 100% | 7% | 22% | 100% | 26% |
| + | + | + | + | + | + | + |  |  |  |  | 100% | 79% | 55% | 100% | 83% |
| + | + | + | + | + | + |  | + |  |  |  | 100% | 79% | 55% | 100% | 83% |
| + | + |  | + | + | + | + | + |  |  |  | 100% | 69% | 46% | 100% | 75% |
| + | + |  | + | + | + | + |  | + |  |  | 100% | 65% | 46% | 100% | 75% |
| + |  | + | + | + | + | + | + |  |  |  | 100% | 67% | 44% | 100% | 74% |
| + |  | + | + | + | + | + |  | + |  |  | 100% | 67% | 44% | 100% | 74% |
|  |  |  |  | + | + |  | + | + | + | + | 100% | 10% | 22% | 100% | 28% |
|  |  |  |  |  | + | + | + | + | + | + | 100% | 10% | 22% | 100% | 28% |
|  |  |  |  | + | + | + | + | + | + | + | 100% | 7% | 22% | 100% | 26% |

We further tested one example set of the 4-gene panel ($bla_{TEM-1b}$ and $bla_{CARB-2}$, $bla_{CMY-2}$, and ampC) from the 7-gene combination to predict AMP-R in 169 NTS isolates, the specificity is 97% regardless of gene numbers, the sensitivity increased from 44% in one gene ($bla_{TEM-1b}$) to 67% in two-gene panel in three-gene panel, and to 69% in four-gene panel, and accuracy of prediction rates increased from 63% in one gene ($bla_{TEM-1b}$) to 79% in three-gene and four-gene panels (Table 8), supporting the effective prediction of our multigene panel in ampicillin resistance of NTS.

TABLE 8

PCR data from 169 NTS isolates for example sets of the one-gene, two-gene, three-gene, and four-gene prediction for ampicillin resistance.

| $bla_{TEM-1B}$ | $bla_{CARB-2}$ | $bla_{CMY-2}$ | ampC | Specificity | Sensitivity | NPV | PPV | Accuracy |
|---|---|---|---|---|---|---|---|---|
| + | | | | 97% | 44% | 50% | 96% | 63% |
| | + | | | 100% | 23% | 42% | 100% | 51% |
| | | + | | 100% | 5% | 37% | 100% | 39% |
| | | | + | 100% | 5% | 37% | 100% | 39% |
| + | + | | | 97% | 67% | 62% | 97% | 78% |
| + | | + | | 97% | 46% | 50% | 96% | 64% |
| + | | | + | 97% | 47% | 51% | 96% | 65% |
| + | + | + | | 97% | 69% | 63% | 97% | 79% |
| + | + | | + | 97% | 69% | 63% | 97% | 79% |
| + | + | + | + | 97% | 69% | 63% | 97% | 79% |

The above description merely relates to preferred embodiments in the present invention, and it should be pointed out that, for a person of ordinary skill in the art, some improvements and modifications can also be made under the premise of not departing from the principle of the present invention, and these improvements and modifications should also be considered to be within the scope of protection of the present invention.

REFERENCES

1. Majowicz S E, Musto J, Scallan E, Angulo F J, Kirk M, O'Brien S J, et al. The global burden of nontyphoidal Salmonella gastroenteritis. Clin Infect Dis. 2010; 50(6): 882-9. doi: 10.1086/650733. PubMed PMID: 20158401.
2. Chi H, Sun W, Chan W T, Lee H C, Fang S B. Pediatric Salmonella enterocolitis in a teaching hospital in Taitung: A four-year analysis. Acta PaediatrTaiwan. 2001; 42(5): 297-300.
3. Huang I F, Wagener M M, Hsieh K S, Liu Y C, Wu T C, Lee W Y, et al. Nontyphoid salmonellosis in taiwan children: clinical manifestations, outcome and antibiotic resistance. J PediatrGastroenterolNutr. 2004; 38(5):518-23.
4. Reddy E A, Shaw A V, Crump J A. Community-acquired bloodstream infections in Africa: a systematic review and meta-analysis. Lancet Infect Dis. 2010; 10(6):417-32. doi: 10.1016/51473-3099(10)70072-4. PubMed PMID: 20510282; PubMed Central PMCID: PMCPMC3168734.
5. Su L H, Chiu C H, Chu C, Ou J T. Antimicrobial resistance in nontyphoid Salmonella serotypes: a global challenge. ClinInfectDis. 2004; 39(4):546-51.
6. Stokes H W, Gillings M R. Gene flow, mobile genetic elements and the recruitment of antibiotic resistance genes into Gram-negative pathogens. FEMS Microbiol-Rev. 2011; 35(5):790-819.
7. Global priority list of antibiotic-resistant bacteria to guide research, discovery, and development of new antibiotics. World Health Organization, 2017 27 Feb. 2017. Report No.

8. Chiou C S, Lin J M, Chiu C H, Chu C H, Chen S W, Chang Y F, et al. Clonal dissemination of the multi-drug resistant Salmonella enterica serovar Braenderup, but not the serovar Bareilly, of prevalent serogroup C1 Salmonella from Taiwan. BMC Microbiol. 2009; 9:264. doi: 10.1186/1471-2180-9-264. PubMed PMID: 20017951; PubMed Central PMCID: PMCPMC2806260.
9. Surveillance Report of Antimicrobial Resistance in Salmonella spp. in Taiwan 2016 [in Chinese]. Centers for Disease Control, Ministry of Health and Welfare, ROC (Taiwan). 2017.
10. Chen H M, Wang Y, Su L H, Chiu C H. Nontyphoid Salmonella infection: microbiology, clinical features, and antimicrobial therapy. PediatrNeonatol. 2013; 54(3):147-52.
11. Crump J A, Sjolund-Karlsson M, Gordon M A, Parry C M. Epidemiology, Clinical Presentation, Laboratory Diagnosis, Antimicrobial Resistance, and Antimicrobial Management of Invasive Salmonella Infections. ClinMicrobiolRev. 2015; 28(4):901-37.
12. Baucheron S, Chaslus-Dancla E, Cloeckaert A, Chiu C H, Butaye P. High-level resistance to fluoroquinolones linked to mutations in gyrA, parC, and parE in Salmonella enterica serovar Schwarzengrund isolates from humans in Taiwan. AntimicrobAgents Chemother. 2005; 49(2):862-3.
13. Chiu C H, Su L H, Chu C, Chia J H, Wu T L, Lin T Y, et al. Isolation of Salmonella enterica serotype choleraesuis resistant to ceftriaxone and ciprofloxacin. Lancet. 2004; 363(9417):1285-6.
14. Chiu C H, Su L H, Chu C. Salmonella enterica serotype Choleraesuis: epidemiology, pathogenesis, clinical disease, and treatment. ClinMicrobiolRev. 2004; 17(2):311-22.
15. Uchil R R, Kohli G S, Katekhaye V M, Swami O C. Strategies to combat antimicrobial resistance. J Clin Diagn Res. 2014; 8(7):ME01-4. doi: 10.7860/JCDR/2014/8925.4529. PubMed PMID: 25177596; PubMed Central PMCID: PMCPMC4149102.
16. Parry C M, Threlfall E J. Antimicrobial resistance in typhoidal and nontyphoidal salmonellae. Curr Opin Infect Dis. 2008; 21(5):531-8. doi: 10.1097/QCO.0b013e32830f453a. PubMed PMID: 18725804.
17. Lewis K. Platforms for antibiotic discovery. Nat-RevDrug Discov. 2013; 12(5):371-87.
18. Gupta S K, Padmanabhan B R, Diene S M, Lopez-Rojas R, Kempf M, Landraud L, et al. ARG-ANNOT, a new

27 bioinformatic tool to discover antibiotic resistance genes in bacterial genomes. Antimicrob Agents Chemother. 2014; 58(1):212-20. doi: 10.1128/AAC.01310-13. PubMed PMID: 24145532; PubMed Central PMCID: PMCPMC3910750.

19. Kleinheinz K A, Joensen K G, Larsen M V Applying the ResFinder and VirulenceFinder web-services for easy identification of acquired antibiotic resistance and *E. coli* virulence genes in bacteriophage and prophage nucleotide sequences. Bacteriophage. 2014; 4(1):e27943. doi: 10.4161/bact.27943. PubMed PMID: 24575358; PubMed Central PMCID: PMCPMC3926868.

20. McArthur A G, Waglechner N, Nizam F, Yan A, Azad M A, Baylay A J, et al. The comprehensive antibiotic resistance database. Antimicrob Agents Chemother. 2013; 57(7):3348-57. doi: 10.1128/AAC.00419-13. PubMed PMID: 23650175; PubMed Central PMCID: PMCPMC3697360.

21. Didelot X, Bowden R, Wilson D J, Peto T E A, Crook D W. Transforming clinical microbiology with bacterial genome sequencing. Nat Rev Genet. 2012; 13(9):601-12. doi: 10.1038/nrg3226. PubMed PMID: 22868263; PubMed Central PMCID: PMCPMC5049685.

22. Wain J, Keddy K H, Hendriksen R S, Rubino S. Using next generation sequencing to tackle non-typhoidal *Salmonella* infections. J Infect Dev Ctries. 2013; 7(1):1-5. doi: 10.3855/jidc.3080. PubMed PMID: 23324813.

23. Mather A E, Reid S W, Maskell D J, Parkhill J, Fookes M C, Harris S R, et al. Distinguishable epidemics of multidrug-resistant *Salmonella Typhimurium* DT104 in different hosts. Science. 2013; 341(6153):1514-7. doi: 10.1126/science.1240578. PubMed PMID: 24030491; PubMed Central PMCID: PMCPMC4012302.

24. Diaz-Sanchez S, Hanning I, Pendleton S, D'Souza D. Next-generation sequencing: the future of molecular genetics in poultry production and food safety. Poult Sci. 2013; 92(2):562-72. doi: 10.3382/ps.2012-02741. PubMed PMID: 23300324.

25. Curiao T, Marchi E, Grandgirard D, Leon-Sampedro R, Viti C, Leib S L, et al. Multiple adaptive routes of *Salmonella enterica Typhimurium* to biocide and antibiotic exposure. BMC Genomics. 2016; 17:491. doi: 10.1186/s12864-016-2778-z. PubMed PMID: 27411385; PubMed Central PMCID: PMCPMC4943003.

26. Dhanani A S, Block G, Dewar K, Forgetta V, Topp E, Beiko R G, et al. Correction: Genomic Comparison of Non-Typhoidal *Salmonella enterica* Serovars *Typhimurium, Enteritidis*, Heidelberg, Hadar and Kentucky Isolates from Broiler Chickens. PLoS One. 2016; 11(2): e0148706. doi: 10.1371/journal.pone.0148706. PubMed PMID: 26854571; PubMed Central PMCID: PMCPMC4746026.

27. Chuang Y C, Yang C H, Lin J H, Wang K C, Cheng C P, Yeh K S. Primers specific for the fimbrial major subunit gene stdA can be used to detect *Salmonella enterica* serovars. J Food Prot. 2008; 71(6):1108-13. PubMed PMID: 18592734.

28. Bush K, Jacoby G A. Updated functional classification of beta-lactamases. Antimicrob Agents Chemother. 2010; 54(3):969-76. doi: 10.1128/AAC.01009-09. PubMed PMID: 19995920; PubMed Central PMCID: PMCPMC2825993.

29. Novais A, Canton R, Valverde A, Machado E, Galan J C, Peixe L, et al. Dissemination and persistence of blaCTX-M-9 are linked to class 1 integrons containing CR1 associated with defective transposon derivatives from Tn402 located in early antibiotic resistance plasmids of IncHI2, IncP1-alpha, and IncFI groups. Antimicrob Agents Chemother. 2006; 50(8):2741-50. doi: 10.1128/AAC.00274-06. PubMed PMID: 16870767; PubMed Central PMCID: PMCPMC1538643.

30. Sparham S J, Kwong J C, Valcanis M, Easton M, Trott D J, Seemann T, et al. Emergence of multidrug resistance in locally-acquired human infections with *Salmonella Typhimurium* in Australia owing to a new clade harbouring blaCTX-M-9. Int J Antimicrob Agents. 2017; 50(1): 101-5. doi: 10.1016/j.ijantimicag.2017.02.014. PubMed PMID: 28476613.

31. Giuriatti J, Stefani L M, Brisola M C, Crecencio R B, Bitner D S, Faria G A. *Salmonella Heidelberg*: Genetic profile of its antimicrobial resistance related to extended spectrum beta-lactamases (ESBLs). Microb Pathog. 2017; 109:195-9. doi: 10.1016/j.micpath.2017.05.040. PubMed PMID: 28578094.

32. McDermott P F, Tyson G H, Kabera C, Chen Y, Li C, Folster J P, et al. Whole-Genome Sequencing for Detecting Antimicrobial Resistance in Nontyphoidal *Salmonella*. Antimicrob Agents Chemother. 2016; 60(9):5515-20. doi: 10.1128/AAC.01030-16. PubMed PMID: 27381390; PubMed Central PMCID: PMCPMC4997858.

33. Bauernfeind A, Stemplinger I, Jungwirth R, Mangold P, Amann S, Akalin E, et al. Characterization of beta-lactamase gene blaPER-2, which encodes an extended-spectrum class A beta-lactamase. Antimicrob Agents Chemother. 1996; 40(3):616-20. PubMed PMID: 8851581; PubMed Central PMCID: PMCPMC163168.

34. Bialvaei A Z, Pourlak T, Aghamali M, Asgharzadeh M, Gholizadeh P, Kafil H S. The Prevalence of CTX-M-15 Extended-spectrum beta-Lactamases Among *Salmonella* spp. and *Shigella* spp. Isolated from three Iranian Hospitals. Eur J Microbiol Immunol (Bp). 2017; 7(2):133-7. doi: 10.1556/1886.2017.00004. PubMed PMID: 28690880; PubMed Central PMCID: PMCPMC5495085.

What is claimed is:

1. A method for detecting ampicillin-resistant (AMP-R) non-typhoidal *Salmonella* (NTS) in a sample from a patient, comprising
    (a) collecting the sample from the patient;
    (b) extracting DNA from the sample;
    (c) performing a polymerase chain reaction (PCR) using the extracted DNA to detect, in the sample, the presence of a combination of a plurality of genes wherein the plurality of genes—consist of a blaTEM-1b gene, a blaCARB-2 gene, and optionally one or more genes selected from the group consisting of a blaCMY-2 gene, blaOXA-1 gene and an ampC gene, wherein the performing a PCR produces amplified copies of each gene of the combination of said plurality of genes and/or amplified fragments of each gene of the combination of said plurality of genes, thereby detecting AMP-R NTS in said sample.

2. The method of claim 1, wherein before extracting the DNA a universal gene for NTS is detected to confirm that the sample contains NTS.

3. The method of claim 2, wherein the universal gene for NTS is stdA.

4. The method of claim 1, wherein the sample is a fecal sample or a body fluid sample.

5. A method for detecting a combination of genes from ampicillin-resistant (AMP-R) non-typhoidal *Salmonella* (NTS) in a sample from a patient, comprising (a) collecting the sample from the patient;

(b) extracting DNA from the sample;

(c) performing a polymerase chain reaction (PCR) using the extracted DNA to detect, in the sample, the presence of nucleic acids from a combination of genes, wherein the combination of genes consists of a $bla_{TEM-1b}$ gene, a $bla_{CARB-2}$ gene, and optionally one or more genes selected from the group consisting of a $bla_{CMY-2}$ gene, and an ampC gene, wherein the performing a PCR produces amplified copies of each gene of the combination of said plurality of genes, and/or amplified fragments of each gene of the combination of genes, thereby detecting AMP-R NTS in said sample.

6. A method for treating a patient having an ampicillin-resistant non-typhoidal *Salmonella* infection, which comprises detecting a combination of genes from ampicillin-resistant (AMP-R) non-typhoidal *Salmonella* (NTS) in a sample from the patient, comprising (a) collecting the sample from the patient;

(b) extracting DNA from the sample;

(c) performing a polymerase chain reaction (PCR) using the extracted DNA to detect, in the sample, the presence of a combination of genes, wherein the combination of genes consists of a $bla_{TEM-1b}$ gene, a $bla_{CARB-2}$ gene, and optionally one or more genes selected from the group consisting of a $bla_{CMY-2}$ gene, and an ampC gene; and (d) administering an antibiotic other than ampicillin to the patient from whom said sample was collected in which said combination of genes were detected.

7. The method according to claim 5, wherein said combination of genes consists of a blaTEM-1b gene, a blaC-ARB-2 gene, and a blaCMY-2 gene.

8. The method according to claim 6, wherein said combination of genes consists of a blaTEM-1b gene, a blaC-ARB-2 gene, and a blaCMY-2 gene.

9. The method according to claim 5, wherein said combination of genes consists of a blaTEM-1b gene, a blaC-ARB-2 gene, a blaCMY-2 gene and an ampC gene.

10. The method according to claim 6, wherein said combination of genes consists of a blaTEM-1b gene, a blaCARB-2 gene, a blaCMY-2 gene and an ampC gene.

* * * * *